United States Patent [19]
Wheeler

[11] Patent Number: 5,594,158
[45] Date of Patent: Jan. 14, 1997

[54] PROCESSES FOR PRODUCING DOXORUBICIN, DAUNOMYCINONE, AND DERIVATIVES OF DOXORUBICIN

[75] Inventor: Desmond M. S. Wheeler, Lincoln, Nebr.

[73] Assignee: The Board of Regents of the University of Nebraska, Lincoln, Nebr.

[21] Appl. No.: 915,466

[22] Filed: Jul. 16, 1992

Related U.S. Application Data

[63] Continuation-in-part of Ser. No. 542,902, Jun. 22, 1990, Pat. No. 5,200,513.

[51] Int. Cl.$^6$ .................................................. C07H 15/24
[52] U.S. Cl. .............................................. 552/201; 552/206
[58] Field of Search ................................. 552/701, 706

[56] References Cited

U.S. PATENT DOCUMENTS

| | | | |
|---|---|---|---|
| 4,515,720 | 5/1985 | Hauser et al. | 552/201 |
| 5,001,243 | 3/1991 | Fischer et al. | 552/706 |

OTHER PUBLICATIONS

*Studies in the Synthesis of Adriamycin*, D. Wheeler, et al., "New Trends In Natural Products Chemistry", 1986, pp. 565–583.

*A Short and Efficient Synthesis of 11–Deoxyanthracyclinones: Strong Base–Induced Cycloaddition of the Suitably Substituted Tetrahydrohomophthalic Anhydride*, Y. Tamura, et al., "Tetrahedron Letters", vol 26, No. 12, pp. 1549–1552, 1985.

*Conjugate Addition of Acylate–Nickel Complexes to Quinone Monoketals: Formal Synthesis of the Naphthoquinone Antibiotics Nanaomycin A and Deoxyfrenolicin*, M. F. Semmelhack, et al., "J. Org. Chem.", vol. 50, 1985, pp. 5566–5574.

*Primary Examiner*—C. Warren Ivy
*Assistant Examiner*—Raymond Covington
*Attorney, Agent, or Firm*—Vincent L. Carney

[57] ABSTRACT

Daunomycinone is a known precursor of the well known antibiotic and antineoplastic, doxorubicin. Daunomycinone may be synthesized by preparing mono ketal of a 1,4-naphthoquinone as the precursor of the CD rings of daunomycinone followed by preparing a precursor for ring A with $C_6$ and $C_{11}$ attached and the stereochemistry at $C_7$ and $C_9$ established and coupling it to CD and then completing ring B.

23 Claims, No Drawings

PROCESSES FOR PRODUCING DOXORUBICIN, DAUNOMYCINONE, AND DERIVATIVES OF DOXORUBICIN

RELATED CASES

This application is a continuation-in-part application of United States application Ser. No. 07/542,902 filed Jun. 22, 1990, in the name of Desmond M. S. Wheeler for Processes for Producing Doxorubicin, now U.S. Pat. No. 5,200,513. Daunomycinone, and Derivatives of Doxorubicin.

BACKGROUND OF THE INVENTION

This invention relates to a process for producing doxorubicin (adriamycin), and derivatives of doxorubicin, through a novel synthesis of daunomycinone and its derivaties. These mycinones can be coupled by known methods to daunosamine to produce doxorubicin and its corresponding derivatives.

It is known that doxorubicin is isolated from *Streptomyces peucetius*. A suitable process for this isolation is described by F. Arcamone, in "Duxorubicin Anticancer Antibiotics," (Academic Press, New York (1981). Moreover, synthetic routes to doxorubicin are known and these are summarized, for example, by F. Arcamone (loc. cit.), K. Krohn, *Angew. Chem. Int. Ed. Engl.*, volume 25 (1986), page 790 and *Tetrahedron*, volume 46 (1989), page 291 and T. R. Kelly, *Tetrahedron Symposium-in-Print*, volume 40 (1984), pages 4537–4793.

A representative prior art procedure for converting daunomycinone to adriamycin is that proposed by Arcamone et al., U.S. Pat. No. 3,803,124. The prior art methods of obtaining daunomycinone have the disadvantage of being expensive.

SUMMARY OF THE INVENTION

It is an object of the invention to provide a novel synthesis of doxorubicin.

It is a still further object of the invention to provide a novel process for synthesis of derivatives of doxorubicin.

It is a still further object of the invention to provide a novel process for the synthesis of doxorubicin and its derivatives in which the A ring is made stereo selectively with its functionality already established and then joined to the CD portion, with the relationship between the C-7 and C-9 hydroxyls established stereoselectively before the tetracyclic skeleton is constructed.

It is a still further object of the invention to provide a novel process for the synthesis of daunomycinone that proceeds in DCAB order with the B ring formed last.

It is a still further object of the invention to provide a novel process of producing intermediates for the synthesis of daunomycinone, namely, methyl 3alpha,5alpha-dihydroxy-5beta-(trimethylsilylethynyl)-2alpha-nitromethylcyclohexane-1beta-carboxylate and the 3,5-acetonide of methyl 3alpha,5alpha-dihydroxy-5beta-(tri-methylsilylethynyl)-2alpha-nitromethylcyclohexane-1beta-carboxylate.

It is a still further object of the invention to provide novel synthetic routes to daunomycinone and derivatives of this compound.

In accordance with the invention a novel synthesis of daunomycinone is provided in which the A-ring precursor of the compound is synthesized from m-anisic acid. The A-ring precursor, methyl cis-2,3-epoxy-5-hydroxy-5-(trimethylsilylethynyl)-cyclohexane-1-carboxylate, is converted to methyl cis-3,5-dihydroxy-5-(trimethylsilylethynyl)cyclohex-1-ene-1-carboxylate which is nitromethylated to produce the required 2alpha-nitromethyl compound. The 3,5-acetonide of the 2alpha-nitromethyl compound is coupled with a 4-mono ketal of a juglone alkyl ether and cyclized to a tetracyclic intermediate. The latter can be converted to daunomycinone and many of its derivatives.

More specifically, this process for the production of daunomycinone, comprises the steps of: (1) condensing methyl 3alpha,5alpha-dihydroxy-5beta-(trimethylsilylethynyl)-2alphanitromethylcyclohexane-1beta-carboxylate acetonide with 1,4-dihydro-4,4,5-trimethoxy-1-oxonaphthalene in the presence of 1,8-diazabicyclo[5.4.0]-undec-7-ene in an aprotic solvent to produce a 3-[(2beta-carbomethoxy-4beta-ethynyl-4alpha,6alpha-(di-O-isopropylidene)-cyclohexanyl-1-yl]-nitromethyl-4,4,5-trimethoxy-1-oxo-1,2,3,4-tetrahydronaphthalene; (2) cyclizing the thus-produced 1-oxotetrahydronaphthalene to produce 7alpha,9alpha-(di-O-isopropylidenyl)-7beta-ethynyl-12-hydroxy-6-nitro-4,5, 5-trimethoxy-5,5a,6,6a,7,8,9,10,10a,11-decahydro-11-naphthacenone; (3) converting the decahydro-11-naphthacenone to 4,5-dimethoxy-7alpha,9alpha-(di-O-isopropylidenyl)-9beta-ethynyl-12-hydroxy-6-nitro-6,6a,7,8,9,10,10a,11-octahydro-11-naphthacenone; (4) oxidizing the thus produced octahydro-11-naphthacenone to 7alpha-9alpha-(di-O-isolpropylidenyl)-9beta-ethynyl-11-hydroxy-4-methoxy-6-nitro-7,8,9,10-tetrahydro-5-12-naphthacenedione; (5) hydrolysing the tetrahydro-5,12-naphthacenedione to 6-desoxy-6-nitro-daunomycinone; (6) reducing the nitro compound to 6-desoxy-6-aminodaunomycinone; (7) diazotising the amino compound and obtaining from it by standard reactions, daunomycinone, the 6-desoxy-6-halo and cyanodaunomycinones and compounds derived from them.

To produce the methyl 3alpha,5alpha-dihydroxy-2alpha-nitromethyl-5beta-(trimethylsilylethynyl)-cyclohexane-1beta carboxylate, methyl cis-3,5-dihydroxy-5-(trimethylsilylethynyl)-cyclohex-1-ene-1-carboxylate is reacted with nitromethane in the presence of 1,8-diazabicyclo[5.4.0]undec-7-ene or sodium hydride as well as a hydrogen bond acceptor, e.g. dimethylsulfoxide or trimethylamine-N-oxide.

To synthesize methyl cis-3,5-dihydroxy-5-(trimethylsilylethynyl)cyclohex-1-ene-1-carboxylate, m-anisic acid is subjected to the Birch reduction with lithium in ammonia to produce 5-oxocyclohex-2-ene-1-carboxylic acid, followed by methylation of thus-produced cyclohex-2-ene-1-carboxylic acid to methyl 5-oxocyclohex-2-ene-1-carboxylate with diazomethane, trimethylsilyl-ethynylation of thus-produced cyclohex-2-ene-1-carboxylate with cerium dichloride trimethylsilylacetylene to produce methyl cis-5-hydroxy-5-(trimethylsilylethynyl)cyclohex-2-ene-1-carboxylate, conversion to an epoxide and opening of the resulting epoxide ring to produce the cis-3,5-dihydroxy compound.

In this process for synthesizing daunomycinone there are several especially significant procedural steps that increase yield greatly, such as: (1) the reaction mixture is kept between −20 to 20 degrees centigrade during esterification with diazomethane; (2) any ethanol and water present in the esterification reaction mixture is removed by azeotropic distillation with benezene to produce methyl ester; (3) methyl ester is immediately treated with cerium dichloride trimethylsilylacetylene at a low temperature, such as −50 to −78 degrees centigrade, to prevent formation of a lactone; (4) the epoxide is formed by oxidation with tert.-butylhydroperoxide in the presence of molybdenum hexacarbonyl catalyst and 4A molecular sieves and the epoxide that is produced is isolated; and (5) the thus-formed epoxide ring is opened with 1,8-diazabicyclo[5.4.0]-undec-7-ene or sodium methoxide in methanol. The cerium reagent should be added to the keto ester to avoid a migration of the double bond.

A feature of the synthesis is the production of the 4,4-dimethylacetal of 5-alkoxy-1,4-naphthoquinones by oxidation of 5-alkoxy-1-naphthol with iodobenzene diacetate in methanol. The preparation of the 5-alkoxy-1-naphthol, in which the alkoxy is of 1–6 carbon atoms, is described in Moore, H. W.; Lee, S.; Rutolo, D.; Sheldon, R., *J. Org. Chem.*, 1978, 43, 2304–2306. Generally, this process may include the steps of: (1) alkylating 1,5-dihydroxynaphthalene with an excess of alkyl iodide in the presence of a base, e.g. potassium carbonate in an aprotic solvent to produce 1,5-dialkoxynaphthalene; (2) dealkylating the thus-produced 1,5-dialkoxynaphthalene with an alkali metal alkanethiolate to remove selectively one alkyl moiety; and (3) acidifying the alkoxide that is produced to form 5-alkoxy-1-naphthol.

As can be understood from the above description, the processes of this invention permit the manufacture of doxorubicin less expensively and permit the effective preparation of derivatives thereof.

DETAILED DESCRIPTION

In the synthesis of daunomycinone, a precursor for rings CD and a precursor for ring A are first synthesized. The precursor for ring A is attached to the precursor for rings CD and ring B is completed after ring A is coupled to rings CD.

More specifically, the precursor for ring A is prepared with $C_6$ and $C_{11}$ attached and the stereochemistry at $C_7$ and $C_9$ established before it is coupled to CD and ring B is completed after the precursor for ring A is coupled to CD. The precursor for the A ring with $C_6$ and $C_{11}$ attached and the stereochemistry at $C_7$ and $C_9$ established, has the general structure shown in formula 1, wherein W is an ester or similar group capable of acting as an electron pair acceptor in a Claisen condensation and related reactions; X is an umpolung equivalent of an acetyl group such as acetylide, trimethylsilylacetylide, ethyl or methyl vinyl ether, 2-methyl-1,3-dithiane or corresponding dithioacetal or dithioacetal oxide, or cynaohydrin silyl ether or related compounds; Y is 2H, or if needed, a suitable protecting group for a 1,3 diol, such as a cyclic ketal e.g. acetonide or a cyclic

STRUCTURAL FORMULA 1

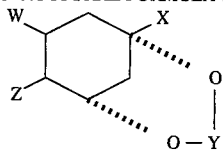

STRUCTURAL FORMULA 2

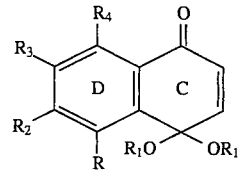

STRUCTURAL FORMULA 3

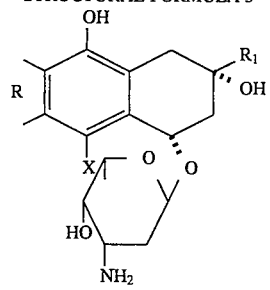

ester e.g. boronate or carbonate; and Z is a one carbon umpolung of carbonyl such as nitromethyl.

In the preferred embodiment, the precursor for ring A is prepared by methylation of 5-oxocyclohex-2-enecarboxylic acid to methyl 5-oxocyclohex-2-enecarboxylate at a reaction temperature of between −20 to 20 degrees centigrade, trimethylsilylethynylation of said cyclohexenecarboxylate at a temperature of between −50 to −78 degrees centigrade after removal of water and ethanol to produce methyl cis-5-hydroxy-5-(trimethylsilylethynyl)cyclohex-2-ene-carboxylate, epoxidation to methyl cis-(2,3-epoxy-5-hydroxy)-5-(trimethylsilylethynyl)cyclohexane-1-carboxylate and opening of the resulting epoxide ring to give methyl cis-3,5-dihydroxy-5-(trimethylsilylethynyl)cyclohex-1-ene carboxylate. This example of the synthesis of the intermediate, required for elaboration of the A-ring, 3alpha,5alpha-dihydroxy-2alpha-nitromethyl-5beta-(trimethylsilylethynyl)cyclohexane-1beta-carboxylate acetonide is shown in charts 1 and 2. It has been found that an approximate 70 percent overall yield of methyl

CHART 1

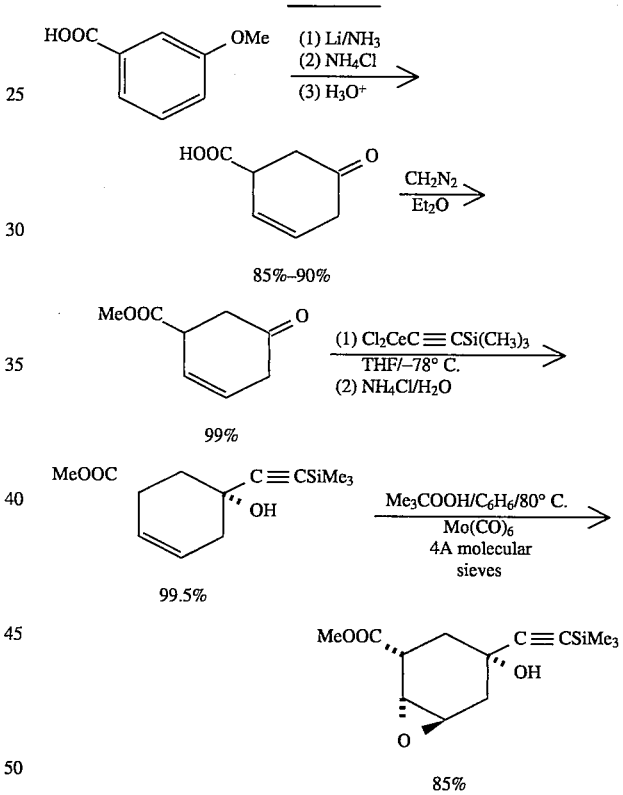

CHART 2

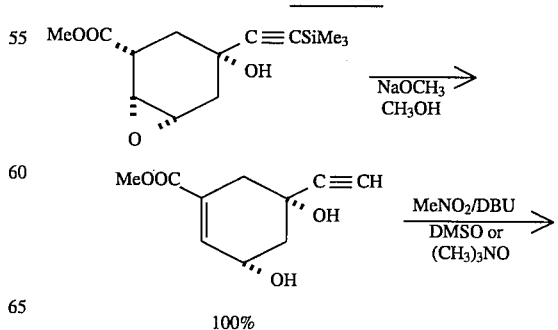

-continued
CHART 2

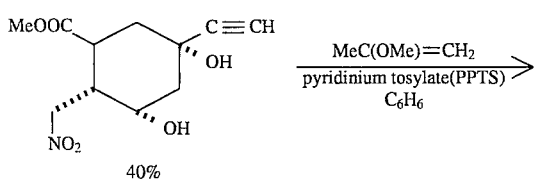

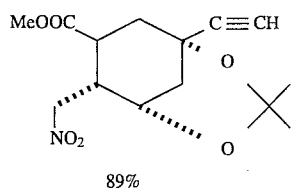

cis-3,5-dihydroxy-5-(trimethylsilylethynyl)cyclohex-1-ene-1-carboxylate from m-anisic acid can be obtained by keeping the reaction mixture cold during esterification with diazomethane and removing any ethanol and water present in the esterification reaction mixture by azeotropic distillation with benzene; quickly reacting to the thus-produced methyl ester with added cerium dichloride trimethylsilylacetylide at a low temperature to prevent formation of a lactone; forming the epoxide by oxidation with cumene hydroperoxide and titanium tetraisoperoxide at room temperature or preferably with tert.-butyl hydroperoxide in refluxing benzene solution in the presence of molybdenum hexacarbonyl catalyst and 4A molecular sieves and isolating the thus-produced epoxide and opening the thus-formed epoxide ring with 1,8-diazabicyclo-[5.4.0]-undec-7-ene or preferably by sodium methoxide in methanol. Without the recited precautions and using completely anhydrous cerium dichloride, the yield from m-anisic acid is less than 10 percent.

Methyl 3alpha,5alpha-dihydroxy-2alpha-nitromethyl-5beta-(trimethylsilylethynyl)-cyclohexane-1beta-carboxylate was obtained from methyl cis-2,3-epoxy-5-hydroxy-5-(trimethylsilylethynyl)cyclohexane-1-carboxylate or methyl cis-3,5-dihydroxy-5-(trimethylsclyethynyl)cyclohexen-1-ene-1-carboxylate by reaction with nitromethane in the presence of 1,8-diazabicyclo-[5.4.0]-undec-7-ene and a hydrogen bond acceptor. Alternatively and better, methyl 3alpha,5alpha-dihydroxy-5beta-ethynyl-2-alphanitromethyl cyclohexane-1beta-carboxylate was obtained from methyl cis-3,5-dihydroxy-5-cyclohex-1-ene-1-carboxylate-and nitromethane in the presence of hydrogen bond acceptor and sodium hydride or 1,8-diazabicyclo[5.4.0.]-undec-7-ene.

The hydrogen bond acceptor used for the nitromethylation reaction may be selected from the following: hexamethylphosphoramide, dimethyl sulfoxide and NN'-dimethyl-NN'propylene urea or other hydrogen bond acceptors such as trimethylamine-N-oxide or corresponding phosphorous or arsenic compounds. The preferred acceptor is dimethyl sulfoxide, the more preferred acceptor is trimethyl amine-N-oxide. Nitromethane also adds to the 3,5-di-(terbutyldimethylsilyl) ether of the diol. The nitromethylation is conveniently carried out at ambient temperature for a time necessary to complete the reaction. The required time is of the order of 2 to 24 hours. If the reaction becomes exothermic, cooling to 15 to 25 degrees centigrade is preferred.

An acetonide is formed from 3alpha,5alpha-dihydroxy-5beta-(trimethylsilylethynyl)-2alpha-nitromethylcyclohexane-1beta-carboxylate by treatment with an acetonide-forming reagent. Representative acetonide-forming agents include, but are not limited to, 2-methoxypropene. Preferably, the acetonide-forming reagent is 2-methoxypropene.

The acetonide-forming reaction is carried out in the presence of a catalyst, such as pyridinium tosylate or p-toluenesulfonic acid. A preferred catalyst is pyridinium tosylate.

An inert solvent is used for the reaction. Benzene, heptane, toluene are representative of solvents suitable for the reaction. When benzene is used as the solvent, the reaction goes to completion within a few minutes' heating under reflux. Conditions appropriate for other solvents can be determined by routine experimentation.

The precursor of the CD rings is generally a mono ketal of a 1,4-naphthoquinone such as shown in structural formula 2, wherein R is one of $OCH_3$ or OH or H, and the $R_1$ groups are dialkyl or $—CH_2—CH_2—$, $R_2$, $R_3$, and $R_4$ are H or $R_2$ and $R_3$ are both alkyl or halo and $R_1$ and $R_4$ are both H or $R_1$ and $R_4$ are both alkyl or halo and $R_2$ and $R_3$ are H.

Preferably the naphthoquinone is the mono ketal in which R and $R_1$ are $CH_3$ and $R_2$, $R_3$ and $R_4$ are H. In the preferred embodiment, the synthesis of a representative 1,4-dihydro-4,4,5-trimethoxy-1-oxonaphthalene is shown in chart 3. The initial steps of the synthesis include alkylation of both hydroxyl groups of 1,5-dihydroxynaphthalene, followed by selective removal of only one alkyl to give 5-alkoxy-1-naphthol. The alkyl moiety can be selected from primary alkyls of 1–6 carbon atoms, such as methyl, ethyl and n-propyl. The alkyl iodide is used in an amount in excess of that, required to alkylate both hydroxyl groups. Preferably, a molar ratio in the range of 4:1 to 2.5:1 of alkyl iodide to 1,5-dihydroxynaphthalene, is used. Most preferably, the ratio is about 3.5:1.

The etherification reaction is conducted in the presence of a base, which is normally selected from organic and inorganic bases. Representative bases include, but are not limited to, sodium carbonate, potassium carbonate, sodium hydroxide, potassium hydroxide, pyridine, triethylamine. A preferred base is potassium carbonate. The amount of base

CHART 3

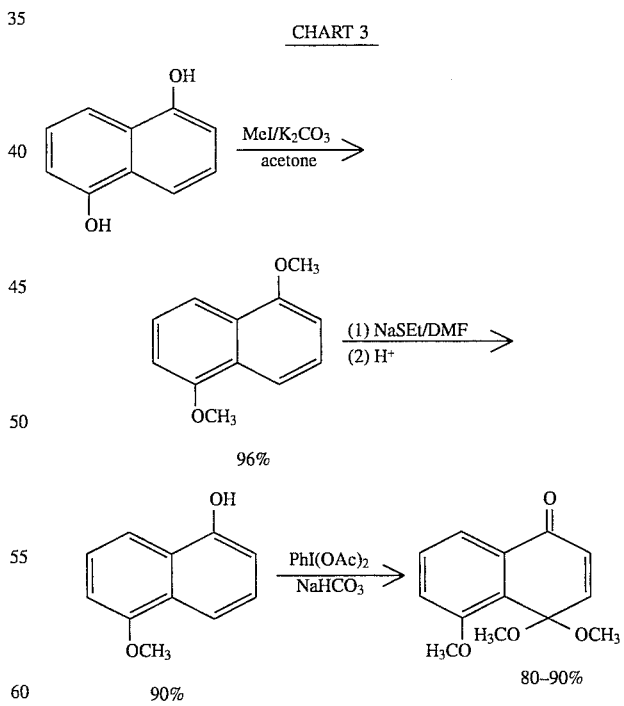

employed should be in the range of 3.5 moles to 4.5 moles, per mole of 1,5-dihydroxynaphthalene.

The aprotic solvent can be selected from acetone, methylethyl ketone, methylisobutyl ketone, tetrahydrofuran, acetonitrile, dimethyl sulfoxide. Preferably, the solvent is acetone.

The alkali metal alkanethiolate, used for removing one alkyl group from the intermediate dialkoxy compound can be selected from sodium and potassium alkanethiolates, having 1–6 carbon atoms in the alkane moiety. Preferably, the alkali metal alkanethiolate is sodium methanethiolate or ethanethiolate. The resulting alkali metal alkoxide can be acidified with any mineral acid, of which sulfuric acid, hydrochloric acid and phosphoric acid are representative.

The 5-alkoxy-1-napthol produced in this way can be converted, for example, to a corresponding juglone alkyl ether 4-ethylene ketal by reaction with ethylene glycol and thallium trinitrate or iodobenzediacetate in methanol and trimethyl orthoformate. A preferred ketal for downstream synthesis is 1,4-dihydro-4,4-ethylenedioxy-5-methoxy-1-oxonaphthalene, produced from 5-methoxy-1-naphthol and ethylene glycol under the conditions stated.

A most preferred product for downstream synthesis is 1,4-dihydro-4,4,5-trimethoxy-1-oxonaphthalene. This is preferably produced from 5-methoxy-1-naphthol by reaction with iodobenzene diacetate in methanol with sodium bicarbonate. It will be understood that alkanols of 2–3 carbon atoms can be used to produce higher ketals by a similar process.

The synthesis of daunomycinone and 6-desoxy-6-nitrodaunomycinone from methyl 3alpha,5alpha-dihydroxy-2alpha-nitromethyl-5beta-(trimethylsilylethynyl)cyclohexane-1beta-carboxylate acetonide and a representative 1,4-dihydro-4,4-5-trimethoxy-1-oxonaphthalene is shown in chart 4. Condensation to the 1-oxotetrahydronaphthalene is carried out in an aprotic solvent. The aprotic solvent may be selected from dimethyl sulfoxide, hexamethylphosphoramide and acetonitrile. Acetonitrile is preferred. The reaction is carried out at ambient temperature. Conversion to a representative intermediate, 3-[(2beta-carbomethoxy-4beta-ethynyl-4alpha,6alpha-(di-O-isopropylidenyl)cyclohexanyl-1-yl]-nitromethyl-4,4,5-trimethoxy-1-oxo-1,2,3,4-tetrahydronaphthalene is complete within 4–6 days.

The thus-produced 1-oxotetrahydronaphthalene is preferably cyclized with an alkali metal alkoxide of 1–6 carbon atoms. Suitable alkoxides can be prepared from alkanols of 1–6 carbon atoms, as above, and an alkali metal hydride. Alkali metal hydrides include sodium hydride or potassium hydride, of which sodium hydride is preferred. Most preferably, the alkali metal alkoxide is sodium methoxide. The cyclization is carried out in an inert solvent, such as benzene, hexane or toluene.

A representative cyclic product of this condensation is 7alpha,9alpha-(di-O-isopropylidenyl)-9beta-ethynyl-12-hydroxy-6-nitro-4,4,-5-trimethoxy-5,5a,6,6a,7,8,9,10,10a,11-decahydro-11-naphthacenone (chart 4).

The thus produced decahydro-11-naphthacenone loses methanol in the presence of an acidic catalyst to yield 7alpha,9alpha-(di-O-isopropylidenyl)-4,5-dimethoxy-9beta-ethynyl-12-hydroxy-6-nitro-6,6a,7,8, 9,10,10a,11-octahydro-11-naphthacenone (chart 5). Possible catalysts include sulfonic acids e.g.

CHART 4

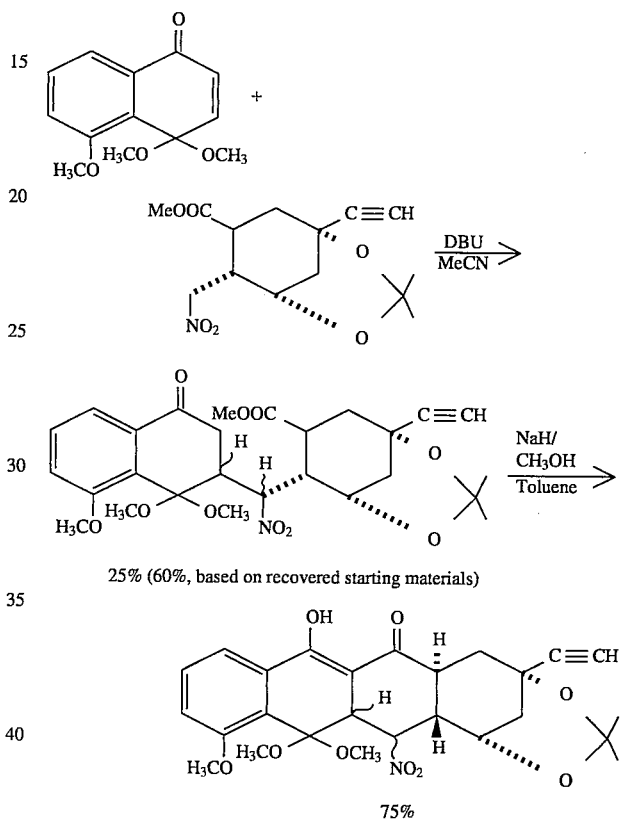

25% (60%, based on recovered starting materials)

CHART 5

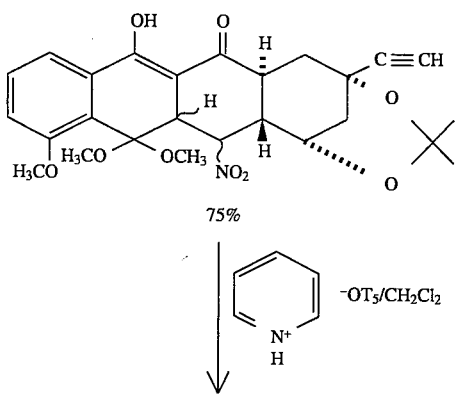

-continued
CHART 5

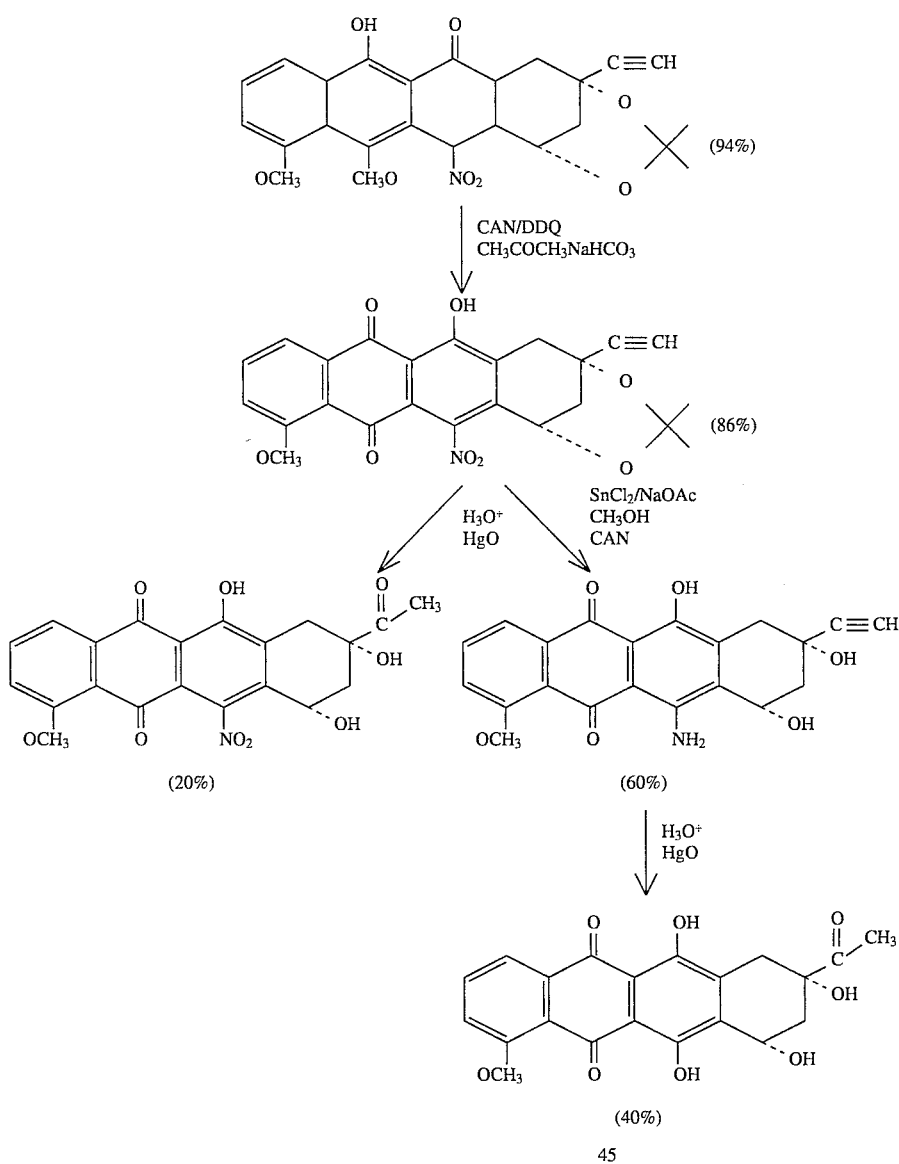

methanesulfonic acid; pyridinium p-toluenesulfonate is preferred. A variety of aprotic solvents e.g. aromatic hydrocarbons, tetrahydrofuran, methylene chloride may be used; methylene chloride is preferred.

In one embodiment, the thus produced octahydro-11-naphthacenone was then oxidized to 7alpha,9alpha(di-O-isopropylidenyl)9beta-ethynyl-11-hydroxy-4-methoxy-6-nitro-7,8,9,10-tetrahydro-5,12-naphthacenedione. Oxidizing agents include cerium ammonium nitrate (CAN) and thallium trinitrate (TTN); solvents include methanol, acetone and acetonitrile. The preferred conditions are CAN in acetone with dichlorodicyanobenzoquinone (DDQ) added in catalytic amount. The thus produced 5,12-naphthacenedione is then hydrolysed with acid in the presence of mercuric oxide to give 6-desoxy-6-nitrodauomycinone (chart 5, example 16).

Additionally, the 6-nitro-5,12-naphthacenedione (chart 5) was converted into 6-amino-7alpha,9alpha-(di-O-isopropylidenyl)-9beta-ethynyl-12-hydroxy-7,8,9,10-tetrahydro-5,12-naphthacenedione by reduction with $SnCl_2H_2O$ in methanol in the presence of sodium acetate at room temperature and the leuco product reoxidized with cerium ammonium nitrate. The amino compound, which can be hydrolyzed to the amino daunomycine, has been converted into its diazonium compound with amyl nitrite in dimethoxyethane and then acid and finally mercuric oxide were added to form daunomycinone (example 18). The diazonium compound can be also converted by standard reactions to 6-desoxy and 6-desoxy-6-halo or cyano daunomycinones. These mycinones can be coupled by known methods to daunosamine to produce daunorubicin and subsequently doxorubicin and their corresponding derivatives shown generally in structural formula 3, wherein R is rings C and D of daunorubicin or doxorubicin or one of their derivatives $R_1$ is one of $COCH_2OH$ or $COCH_3$ and X is $NO_2$, $NH_2$, Hal, CN or H.

In this embodiment, the aprotic solvent for condensing the acetonide with 1,4-dihydro-4,4,5-trimethoxy-1-oxonaphthalene is acetonitrile; the thus-produced 1-oxotetrahydronaphthalene is cyclized with sodium hydride in the presence of a catalytic quantity of methanol in toluene; the thus-produced decahydro-11-naphthacenone is converted to the octahydro-11-naphthacenone in an acidic medium; the thus-produced octahydro-11-naphthacenone is oxidized to the tetrahydro- 5,12-naphthacenedione with the thus-produced tetrahydro-5,12-naphthacenedione being converted to 6-desoxy-6-nitrodaunomycinone by hydrolysis and hydration and into daunomycinone and 6 to 8 daunomycinones in which the substituent at $C_6$ has been changed.

In a further embodiment (chart 6), the aprotic solvent for condensing the acetonide with 1,4-dihydro-4,4,5-trimethoxy-1-oxonaphthalene is acetonitrile; the thus-produced 1-oxotetrahydronaphthalene is cyclized with sodium methoxide; the thus-produced decahydro-11-naphthacenone is converted to 9beta-acetyl-4,5-dimethoxy-6-nitro-7alpha,9alpha,12-trihydroxy-6,6a,7,8,9,10,10a,11-octahydro-11-napthacenone by hydrolysis with acid in the presence of mercuric oxide in an acidic medium; the thus-produced 9-beta-acetylocatahydro-11-naphthacenone is oxidized to 7alpha,9-alpha-dihydroxy-4-methoxy-6-nitro-6,6a,7,8,9,10,10a,11-octahydro-5,11,12-naphthacenetrione with thallium nitrate and the produced octahydro-5,11,12-naphthacenetrione is converted to daunomycinone.

In another embodiment, shown in chart 7, instead of oxidizing the octahydro-11-naphthacenone to 7alpha,9alpha-(di-O-isopropylidenyl)9beta-ethynyl-11-hydroxy-4-methoxy-6-nitro-7,8,9,10-

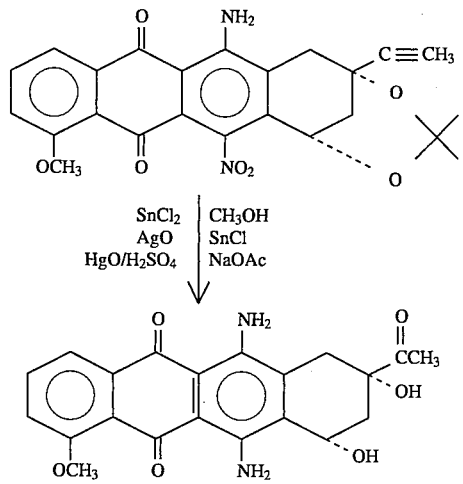

CHART 6

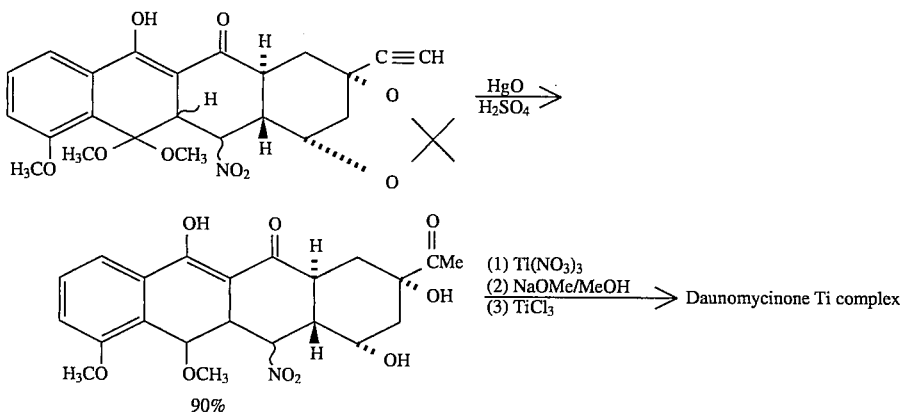

CHART 7

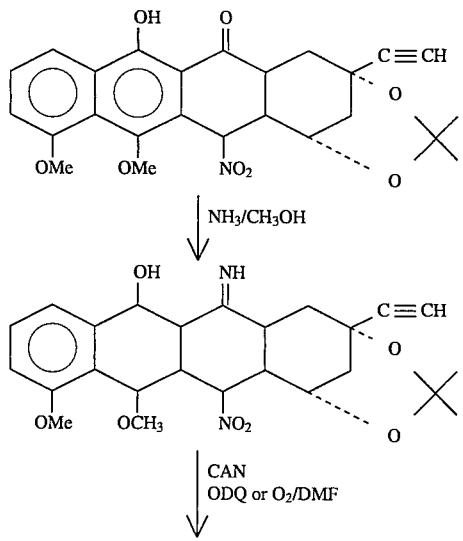

tetrahydro-5,12-naphthacenedione, the nitrooctahydro-11-naphthacenone was treated with ammonia and 25 mL of methanol for 24 hours to yield 4,5-dimethoxy-7alpha,9alpha-(di-O-isopropylidenyl)-9beta-ethynyl-12-hydroxy-11-imino-6-nitro-6,6a,7,8,9,10,10a,11-octahydronaphthacene, which was oxidized with cerium ammonium nitrate in wet THF solution with sodium bicarbonate and a catalytic amount of dichlorodicyanobenzoquinone to yield 11-amino-7alpha,9alpha-(di-O-isopropylidenyl)-9beta-ethynyl-4-methoxy-6-nitro-7,8,9,10-tetrahydro-5,12-naphthacenedione needles in 89 percent yield. Preferably, the same product was obtained in 90 percent yield by refluxing the nitroiminonaphthacene in $O_2$/DMF overnight. Chromatography was not needed.

To obtain 11-amino, 6,11-didesoxy-6-nitrodaunomycinone (as shown in chart 8), the nitroaminonaphthacenedione in THF was hydrolysed with sulfuric acid and mercuric oxide.

Alternatively (chart 7), the nitroaminotetrahydronaphthacenedione was reduced with stannous chloride in methanol with sodium acetate to produce 6,11-diamino-7alpha,9alpha-(di-O-isopropylidenyl)-9beta-ethyl-4-methoxy-7,8,9,10-

CHART 8

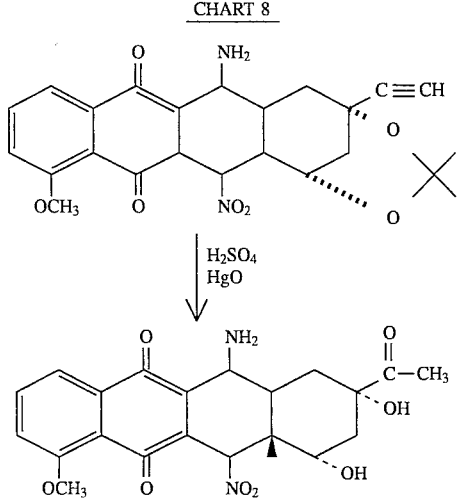

tetrahydro-5,12-naphthacenedione which was then hydrolyzed with acid in the presence of mecuric oxide to 6,11-diamino-6,11-didesoxydaunomycinone (chart 7). These daunomycinones are the first derivatives with two non oxygen groups in ring B.

The amino group in the nitroaminodaunomycinone can be converted by the way of the 11-diazonium salt and standard reactions into halo, cyano and other derivatives (e.g. amides) obtainable from these compouds, thus producing a series of 6-nitrodaunomycinones substituted at $C_{11}$. For example, chart 9 shows the preparation of 11-fluoro-6,11-didesoxy-6-nitrodaunomycinone of example 24.

The 6-nitro group in these compounds can then be reduced to 6-amino and using standard reactions by way of the 6-diazonium compound, into hydroxyl, desoxy, halo or cyano thus giving further daunomycinones substituted at both $C_6$ and $C_{11}$ with different groups. The 6,11-diamino compound can be converted by way of the diazonium compound into 6, 11-disubstituted derivatives (halogen, cyano and functionalities derived from these groups) in which the substitutents at $C_6$ and $C_{11}$ are the same. Thus, the work makes available a large number of 6,11-daunomycinones which can be coupled with daunosamine

CHART 9

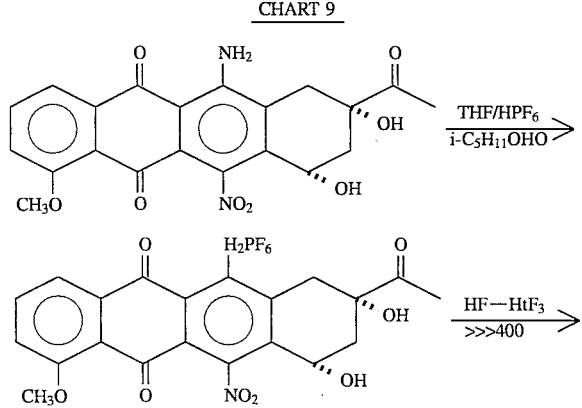

-continued
CHART 9

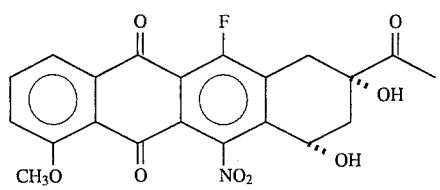

to produce a new series of doxorubicins. Such 6,11-daunomycinones and doxorubicins may take the form shown as formula 4, wherein $R_1$ is one of: $CH_3$ or $CH_2OH$; $R_2$ is one of daunosamine, or H; $R_3$ is one of —OH, $NO_2$, $NH_2$, F, Cl, Br, I, CN and H and groups derived from these; $R_4$ is one of OH, $NO_2$, $NH_2$, F, Cl, Br, I, CN and H or groups derived or substituted for these; and $R_5$ is $OCH_3$, OH, or H, $R_6$ is H, $R_7$ is H and $R_8$ is H. In addition, ring D could have the following substitution: $R_5$ and $R_6$ are H, $R_7$ and $R_8$ are alkyl or halo; or $R_5$ and $R_6$ are alkyl or halo; and $R_7$ and $R_8$ are H.

In this specification, "easily derived 6-analogues and 11-analogues" means analogues in which groups $R_3$ and $R_4$ in structural formula 4 are groups arrived at by known substitution methods for the nitro group at the 6 position or amino groups at the 6 position or 11 position, similar to those disclosed above. For example, the transformation of $R_3$ from $NO_2$ to OH, F, Cl, Br, I and CN is effected by reducing $NO_2$ to $NH_2$ and then converting $NH_2$ to its diazonium salt with nitrite. The diazonium group is then converted to OH by boiling the

STRUCTURAL
FORMULA 4

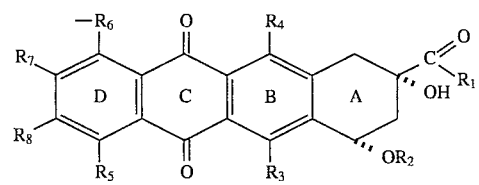

solution and to F by treatment with $HPF_6$ followed by 3HF $(C_2H_3)_3N$ with ultrasound. The other derivatives ($R_3$=Cl, Br, I and CN) are made by treatment of the diazonium salt with CuX (X=Cl, Br, I and CN).

The transformation of $R_4$ from $NH_2$ to OH, F, Cl, Br, I and CN proceeds by: (1) converting $NH_2$ into the diazonium group; (2) boiling the solution to give OH; (3) treatment with $HPF_6$ and then 3HF $(C_2H_3)_3N$ with ultrasound to provide F at the $R_4$ position. Addition of CuX where X=Cl, Br, I and CN provides $R_4$=Cl, Br, I and CN. Modifications in $R_4$ precedes those in $R_3$ except when making $R_3$ the same as $R_4$.

By analogy, the compounds in the disubstituted amines are expected to show anticancer activity. They will also be examined for cardiotoxicity.

EXAMPLES

Without further elaboration it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the following examples, the temperatures are set forth uncorrected in degrees centigrade. Unless otherwise indicated, all parts and percentages are by weight.

Materials and Methods $^1$H NMR spectra were recorded on a Varian EM-390 (90 MHx), a Varian VXR-200 (200MHx) or a Nicolet 1180 WB (360 MHz) spectrometer. Data are reported as chemical shifts in parts per million referenced to trimethylsilane internal standard (0 ppm) or to the residual chloroform peak of deuteriochloroform (7.26 ppm). Multiplicity, number of protons and coupling constants are reported. Couplings and/or coupling constants were determined using the COSY technique or by proton irradiation experiments.

$^{13}$C NMR spectra were obtained on a Varian VXR-200 (50.4 MHz) spectrometer. Chemical shifts are referenced to the center peak of the residual chloroform triplet (77.0 ppm).

Ultraviolet spectra were obtained on a Hewlett-Packard 8450 UV-Vis spectrophotometer.

Infrared absorption spectra were recorded on a Perkin-Elmer Model 283 or an Analect RFX-30 spectrophotometer and are referenced to polystyrene (160 cm$^{-1}$).

Elemental analyses were carried out by Desert Analytics (Tuscon, Ariz.).

Mass spectra were provided by the Midwest Center for Mass Spectrometry, University of Nebraska-Lincoln.

Melting points were determined in open-end capillary tubes on a Mel-Temp apparatus.

Column chromatography was carried out on E. Merck silica gel 60 (Flash, 40–230 mesh) and all thin layer chromatography (TLC) was carried out on commercial silica gel plates (Analtech Silica HLF 250 m or Merck Silica gel 60F 254).

High performance liquid chromatography (HPLC) was performed on a Waters Associates Model 600E chromatography apparatus, equipped with a Waters Associates Model R$_{403}$ Differential Refractometer, using normal-phase silica gel columns.

Solvents were distilled before use over an appropriate drying agent under a nitrogen atmosphere. All reactions requiring anhydrous conditions were done under nitrogen in flame-dried flasks. Solvents were evaporated using a Buchi rotary evaporator, then by evacuation at about 0.10 mm Hg at room temperature.

EXAMPLE 1

5-Oxocyclohex-2-ene-1-carboxylic Acid

The procedure of Biffin et al., *Aust. J. Chem.*, vol. 25 (1972), page 1329, was used.

To a stirred slurry of 30 g (0.21 mol) of m-anisic acid (3-methoxybenzoic acid) in 300 mL of liquid ammonia were slowly added small pieces of lithium (3.5 g, 0.5 mol). Additional lithium (0.5 g, 0.07 mol) was added to maintain the blue color of the solution. The mixture was stirred for 2 hours and then cautiously quenched with solid ammonium chloride (45 g, 0.84 mol).

Ammonia was allowed to evaporate at room temperature. The last traces of ammonia were removed by warming the mixture under aspirator pressure. The resulting residue was dissolved in 200 mL of ice water and acidified to pH 1 with conc HCl. The resulting solution was extracted with four 100-mL portions of ethyl acetate. The combined ethyl acetate extracts were washed with one 50-mL portion of saturated sodium chloride solution, dried over sodium sulfate and evaporated to dryness. Crude semi-crystalline acid (24.1 g) was washed with a small amount of cold ether to yield 5-oxocyclohex-2-ene-1-carboxylic acid, off-white crystals, mp 98–101 degrees centigrade, lit (Biffin et al., supra, 98 to 99 degrees centigrade) yield 80 to 90 percent.

$^1$H NMR (CDCl$_3$): delta values 10.0 (s, 1H, COOH), 5.9 (m, 2H, HC=CH), 3.5 (m, 1H, CHCOO), 2.8 (m, 2H, C=CCH$_2$), 2.5 (m, 2H, CH$_2$).

EXAMPLE 2

Methyl 5-Oxocyclohex-2-ene-1-carboxylate

A solution of 0.7M diazomethane in ether was slowly added to a solution of 6.0 g (42.8 mmol) of 5-oxocyclohex-2-ene-1-carboxylic acid in 100 mL of ether at 0 degrees centigrade, with swirling. The addition of diazomethane was continued until the bubbling ceased and a yellow color persisted. The solution was treated with a rapid stream of nitrogen until the yellow color was discharged. The solvent was removed by evaporation. Benzene (100 mL) was added and evaporated at room temperature using an aspirator. The residue was placed on a vacuum line for 2 hours to produce 6.5 g (42.4 mmol, 99 percent) of methyl 5-oxocyclohex-2-ene-1-carboxylate (oil).

$^1$N NMR (CDCl$_3$): delta values 5.9 (m, 2H, HC=CH), 3.7 (s, 3H, COOMe), 3.5 (m, 1H, HCOO), 2.9 (m, 2H, C=CCH$_2$), 2.7 (m, 2H, CH$_2$).

EXAMPLE 3

Methyl cis-5-Hydroxy-5-(trimethylsilylethynyl)-cyclohex-2-ene-1-carboxylate

A solution of n-butyllithium (2.5M, 16.8 mL, 42.1 mmol) was added dropwise, via a syringe, to a stirred solution of trimethylsilylacetylene (7 mL, 46.8 mmol) in 120 mL of tetrahydrofuran (THF) at –78 degrees centigrade. The resulting slurry was stirred at –78 degrees centigrade for 15 minutes and transferred via a cannula to slurry of 13.45 g (54.6 mmol) of cerium trichloride in 80 mL of THF at –78 degrees centigrade. The cerium chloride had been obtained by drying cerium trichloride heptahydrate (20.4 g, 54.6 mmol) at 140 to 160 degrees centigrade/0.1 mm Hg for 2 hours. Nitrogen was admitted to the cooled flask and 80 mL of dry THF was added to the resulting slurry, which was stirred overnight under nitrogen.

After the addition was complete (45 minutes), the resulting mixture was stirred for 1 hour at –78 degrees centigrade. The organocerium reagent, cerium dichloride trimethylsilylacetylide, was transferred over 45 minutes into a solution of 6.36 g (41.3 mmol) of methyl 5-oxocyclohex-2-ene-1-carboxylate in 80 mL of THF at –78 degrees centigrade. The resulting mixture was stirred for 1 hour more at –78 degrees centigrade and the reaction mixture was poured without warming into 400 mL of 10 percent ammonium chloride solution at 0 degrees centigrade. The resulting mixture was extracted with four 150-mL portions of ether. The combined organic extracts were washed with 200 mL of saturated aqueous sodium chloride solution and dried over sodium sulfate. Evaporation of the solvent yielded 10.04 g (41.1 mmol, 99.5 percent) of methyl cis-5-hydroxy-5-(trimethylsilylethynyl)cyclohex-2-ene-1-carboxylate, an oil.

IR(CH$_2$Cl$_2$): 3585 (COH), 2160 (C≡C), 1721 (COOCH$_3$), 1653 (C=C) cm$^{-1}$.

$^1$NRM(CDCl$_3$): delta values 5.9–5.7 (m, 2H, CH=CH), 3.7 (s, 3H, COOCH$_3$), 3.3 (m, 1H, CHCOO), 2.6 (s, 1H, OH), 2.5 (dd, 1H, C=CCH$_2$), 2.4 (dd, 1H, C=CCH$_2$), 2.2 (m, 2H, CH$_2$), 0.2 (s, 9H, Si(CH$_3$)$_3$).

$^{13}$C NMR (CDCl$_3$): delta values 174.0, 125.3, 123.4, 108.2, 87.4, 65.7, 51.9, 41.2, 39.1, 37.6.

MS, m/e (relative intensity): 252.2116 [M]$^+$ (0.72), 237.0949 [M-CH$_3$]+ (29), 140.0657 (61). HRMS calcd for C$_{13}$H$_{20}$O$_3$Si: 252.1181.

Anal. Calcd for C$_{13}$H$_{20}$O$_3$Si: C, 61.86, H, 7.99. Found: C, 62.10, H, 8.13,

Example 4

Methyl cis-(2,3-Epoxy-5-hydroxy)-5-(trimethylsilylethynyl)cyclohexane-1-carboxylate A solution of tert.-butyl hydroperoxide (25.5 mL, 76.66 mmol 3.0M) in 2,2,4-trimethylpentane was added to a stirred mixture of molybdenum hexacarbonyl (207 mg, 0.784 mmol), methyl cis-5-hydroxy-5-(trimethylsilylethynyl)cyclohex-2-ene-1-carboxylate (5 g, 19.16 mmol) and 4A activated molecular sieves) in 100 mL of benzene. The mixture was then heated under reflux for 18 hours and (CH$_3$)$_2$S was added. The mixture was filtered and the residue washed with ethyl acetate (100 mL). The combined organic solutions were washed with water (3×100 mL) and the aqueous layer was re-extracted with CH$_2$Cl$_2$ (2×100 mL). The combined organic layers were dried over sodium sulfate. Evaporation of the solvent gave the crude product (4.5g) as an oil. Flash chromatography of the oil (3:1 hexanes/ethyl acetate v/v) gave crystalline methyl cis-(2,3-epoxy-5-hydroxy)-5-(trimethylsilylethynyl)cyclohexane-1-carboxylate (0:4.3 g, 84 percent), mp. 74.1 to 74.6 degrees centigrade.

IR(KBr): 3360 (OH), 2160 (C≡C), 1732 (C=O), 1260, 845 cm$^{-1}$.

$^1$H NMR (CDCl$_3$): 3.8 (s, 3H, COOCH$_3$), 3.5 (m, 1H, CHCOO), 3.3 (m, 2H, HCOCH), 2.4 (dd, 1H, CH$_2$), 2.3 (s, 1H, OH), 2.0 (d, 1H, CH$_2$), 1.85 (m, 2H, CH$_2$), 0.17 (s, 9H, C≡CSi(CH$_3$)$_3$).

$^{13}$C NMR (CDCl$_3$): 172.45 (COO), 107.43 (SiC≡C), 89.47 (C≡C), 66.26, 52.2, 51.80, 50.71, 40.92, 38.26, 31.03, 0.20 (Si(CH$_3$)$_3$).

MS m/r (relative intensity): 253.0897 (21.8) [M-CH$_3$]$^+$, 236.0871 (38.2) [M-CH$_3$OH]$^+$, 191. 0035 (19.3), 159.0715 (16.6). Calcd for C$_{13}$H$_{20}$O$_4$Si: 253.0896.

Anal. Calcd for C$_{13}$H$_{20}$O$_4$Si: C, 58,18, H, 7.51. Found: C, 58.09, H, 7.65.

Example 5

Methyl cis-3,5-Dihydroxy-5-(trimethylsilylethynyl)cyclohex-1-ene-1-carboxylate

A solution of 92.8 mg (0.345 mmol) of methyl cis-(2,3-epoxy-5-hydroxy)-5-(trimethylsilylethynyl)cyclohexane-1-carboxylate and 52.5 mg (0.345 mmol) of 1,8-diazabicylo-[5.4.0]-undec-7-ene in 10 mL of methylene chloride was stirred for 2 hours at room temperature. The solvent was removed by evaporation and the residue was dissolved in a minimum amount of methylene chloride and filtered through a plug of flash silica gel (1:1 hexanes/ethyl acetate v/v). Evaporation of the solvent yielded methyl cis-3,5-dihydroxy-5-(trimethylsilylethynyl)cyclohex-1-ene-1-carboxylate, a colorless oil, which crystallized on standing, mp 89.8 to 90.8 degrees centigrade.

IR (CH$_2$Cl$_2$): 3310 (OH, 2158 (C≡C), 1721 (COOCH$_3$), 1653 cm$^{-1}$.

$^1$H NMR (CDCl$_3$): delta values 7.1 (s, 1H, C=CH), 4.4 (m, all couplings less than 2 Hz, 1H, CCH(OH)), 3.8 (s, 3H, COOCH$_3$), 3.0–3.4 (m, 1H, OH), 2.9–2.8 (dd, 2H, CH$_2$), 2.6 (s, 1H, OH), 2.5–2.2 (dd, 2H, CH$_2$), 0.17 (s, 9H, C—CSi(CH$_3$)$_3$).

$^1$H NMR (D$_6$DMSO): delta values 7.1 (s, 1H, C=CH), 6.2 (2,1H, OH), 5.6 (d, 1H, OH), 4.7 (bs, 1H, CCHH(OH)), 4.0 (s, 3H, COOCH$_3$), 3.0 (d, J=17 Hz, 1H, C=CCH equatorial), 2.6 (d, J=17 Hz, 1H, C=CCH axial), 2.5 (m, 1H, (HO)CCH axial), 1.9 (dd, J=10, 10 Hz, 1H (HO)CCH axial).

$^{13}$C NMR (CDCl$_3$): 167.20 (C=O), 138.88, 127.60, 108.0, 88.52, 66.04, 61.62, 51.92, 41.74, 38.87, 0.228.

Anal. Calcd for C$_{13}$H$_{20}$O$_4$Si: C, 58.18; H, 7.51. Found: C, 58.24; H, 7.65.

Example 6

Addition of Nitromethane to Methyl cis-3,5-Dihydroxy-5-(trimethylsilylethynyl)cyclohex-1-ene-1carboxylate (i) Methyl cis-3,5-dihydroxy-5-trimethylsilylethynylcyclohex-1-ene-1-carboxylate (5.91 g, 22.0 mmol) was added in one portion to a mixture of nitromethane (12.2 g, 44.0 mmol) and DBU (6.7 g, 22.0 mmol) in 30 mL of dimethyl sulfoxide (DMSO). The mixture was stirred at room temperature for 15 hours and then neutralized to pH 6 with about 20 mL of 6M HCl.

The resulting mixture was extracted with four 100-mL portions of ethyl acetate. The organic phase was washed with 30 mL of saturated aqueous sodium chloride solution and dried over sodium sulfate. Evaporation of the solvent gave a crude oil product (10.0 g), which contained some DMSO.

Flash chromatography in ethyl acetate/hexanes (3:7 v/v) gave methyl 3alpha,5alpha-dihydroxy-5beta-(trimethylsilylethynyl)-2alpha-nitromethylecyclohexane-1beta-1-carboxylate (trans isomer, 0.8321 g, 2.5 mmol, 11.5 percent); methyl 3alpha,5alpha-dihydroxy-5beta-trimethylsilylethynyl-2beta-nitromethylcyclohexane-2beta-carboxylate (the cis isomer, 1.95 g, 5.9 mmol, 26.9 percent); methyl 3alpha,5alpha-dihydroxy-5beta-ethynyl-2alpha-nitromethylcyclohexane-1beta-carboxylate (trans desilylated isomer, 1.52 g. 5.9 mmol, 26.9 percent); methyl 3alpha,5alpha-dihydroxy-5beta-ethynyl-2beta-nitromethylcyclohexane-1beta-carboxylate (cis desilylated isomer, 1.28, 5.0 mmol, 22 percent). The overall yield of nitro adducts was 88 percent.

(ii) Nitromethane (8 mL, 112 mmol) was added to a slurry of sodium hydride (2.4 g, 56 mmol, 50 percent in mineral oil) in 50 mL of dry DMSO. The mixture was cooled as necessary to maintain an internal temperature of 20 degrees centigrade and stirred slowly for 1 hour. Methyl cis-3,5-dihydroxy-5-(trimethylsilylethynyl)cylohex-1-ene-1carboxylate (3.0 g. 11.2 mmol) was added in one portion and the mixture was stirred for 24 hours at room temperature. To the resulting mixture was added 3 mL of conc HCl in ice. Additional HCl was added until the pH reached 7. The mixture was extracted with four 150-mL portions of ether, washed with 100 mL of saturated aqueous sodium chloride solution, dried over sodium sulfate and evaporated to give 3.39 g of residue, which contained some DMSO (TLC).

Flash chromatography in ethyl acetate/hexanes (3:7 v/v) gave 2.12 g of product, characterized as a mixture of diastereomeric methyl 3,5-dihydroxy-5-(trimethylsilylethynyl)-2-nitromethylcyclohexane-1-beta-carboxylates.

Trans isomer (1,021 g, 25.8 percent), methyl 3alpha, 5alpha-dihydroxy-5beta-(trimethylsilylethynyl)-2alpha-nitromethylcyclohexane-1beta-carboxylate:

IR (CH$_2$Cl$_2$): 3421, 2958, 2161, 1737, 1558 cm$^{-1}$.

$^1$H NMR (CDCl$_3$): delta values 4.7–4.6 (dd, 1H, CH$_2$NO$_2$), 4.0–4.1 (m, 1H, CHOH), 3.8 (bs, 2H, OH), 3.7 (s, 3H, COOCH$_3$), 2.8–2.9 (ddd, J=4, 12, 12 Hz, CHCOOCH$_3$). 2.5–2.6 (m, 1H, CHCH$_2$NO2), 2.3–2.4 (m, 2H, CH$_2$ equatorial), 2.0 (dd, J=12, 12 Hz, 1H, CH$_2$ axial), 1.9 (dd, J=12, 3 Hz, 1H, CH$_2$ axial), 0.1 (s, 9H, Si(CH$_3$)$_3$).

$^{13}$C NMR (CDCl$_3$): delta values 173, 128, 106, 87, 75, 67.1, 66.8, 52, 41.5, 41.2, 36.7, 0.3.

Cis isomer (1.101 g, 19.8 percent), methyl 3alpha,5alpha-dihydroxy-5beta-(trimethylsilylethynyl)-2beta-nitromethyl-cyclohexane-1betacarboxylate:

IR (CH$_2$Cl$_2$): 3423, 2956, 2160, 1739, 1556 cm$^{-1}$.

$^1$H NMR (CDCl$_3$): delta values 4.6 (dd, 1H, CH$_2$NO$_2$), 4.1 (m, 1H, CHOH), 3.7 (s, 3H, COOCH$_3$), 2.9 (bs, 2H, OH), 2.0–2.2 (mc, 4H, CH$_2$), 0.2 (s, 9H, Si(CH$_3$)$_3$).

$^{13}$C NMR: delta values 173, 128, 106, 89, 74, 67.7, 67.1, 52, 41, 37, 30, 0.2.

Anal. Calcd for C$_{14}$H$_{22}$O$_6$NSi: C, 51.20, H. 6.75, N, 4.26. Found: C, 51.20; H, 7.19: N, 4.17.

Example 7

Addition of Nitromethane to Methyl cis-(2,3-Epoxy-5-hydroxy)-5-(trimethylsilylethynyl)cyclohexane-1carboxylate Nitromethane (4.2 g, 68 mmol) was added to a solution of 50 mL of DMSO and 5.2 g, (34 mmol) of DBU in 50 mL of DMSO. The mixture was stirred for 5 minutes, after which 1.8 g (6.8 mmol) of solid methyl cis-2,3-epoxy-5-hydroxy-5-(trimethylsilyl- ethynyl)cyclohexane-1-carboxylate was added in one portion. The reaction was followed by TLC, using 1:2 v/v ethyl acetate/hexanes as eluant. After 2 hours, all of the epoxide had been consumed and a new spot, corresponding to diol appeared. After 16 hours, TLC showed that four new products and no starting materials or diol was present.

The reaction mixture was poured into 100 mL of cold 5 percent HCl solution and extracted with four 50-mL portions of ether and with 100-mL of saturated aqueous NaCl solution and dried over sodium sulfate. The ether was evaporated to yield 0.66 g of an oil, which was separated by flash chromatography (1:2 v/v ethyl acetate/hexanes) to yield methyl 3alpha,5alpha-dihydroxy-5beta-(trimethylsilylethynyl)-2alpha-nitromethylcyclohexane-1beta-carboxylate (0.28 g, 12.5 percent, trans nitro diol) and methyl 3alpha, 5alpha-dihydroxy-5beta-(trimethylsilyl-ethynyl)-2beta-nitromethylcyclohexane-1beta-carboxylate (0.31 g, 13.8 percent, cis nitro diol).

The aqueous phase was reextracted with methylene chloride and dried over sodium sulfate. Evaporation of solvent gave 0.52 g of an oil, separated by flash chromatography (1:1 v/v ethyl acetate/hexanes) into two desilylated nitroadducts, methyl 3alpha,5alpha-dihydroxy-5beta-ethynyl-2alpha-nitromethylcyclohexane-1beta-carboxylate (0.25 g, 12.4 percent, trans desilylated isomer) and methyl 3alpha, 5alpha-dihydroxy-5beta-ethynyl-2beta-nitromethylcyclohexane-2beta-carboxylate (0.19 g, 9.4 percent, cis desilylated isomer).

Example 8

Acetonide of Methyl 3alpha,5alpha-Dihydroxy-5beta-(trimethylsilylethynyl)-2alpha-nitromethylcyclohexane-1beta-carboxyate A mixture of 2-methoxypropene (260 microL, 3.6 mmol), trans nitro diol (methyl 3alpha,5alpha-dihydroxy-5beta-(trimethylsilylethynyl)-2alpha-nitromethylcyclohexane-1beta-carboxylate, 1.2 g, 3.6 mmol) and pyridinium tosylate (10 mg, 0.036 mmol) in 100 mL of benzene was stirred for at room temperature for 15 minutes. After 260 microL (3.6 mmol) of additional 2-methoxypropene was added, the resulting mixture was heated under reflux for 5 minutes. The resulting solution was cooled and washed with 30 mL of saturated aqueous sodium bicarbonate solution with 30 mL of saturated aqueous sodium chloride solution and dried over sodium sulfate. Evaporation of solvent yielded 1.22 g (3.22 mmol, 89 percent) of acetonide as an oil.

1R (neat ATR): 2990, 2164, 1735, 1556 cm$^{-1}$.

$^1$H NMR (CDCl$_3$): delta values 4.6–4.5 (dd, 1H, CHNO$_2$), 4.4–4.35 (dd, 1H, CHNO$_2$), 4.25–4.3 (m, 1H, CHOC), 3.7 (s, 3H, COOCH$_3$), 3.0 (ddd, J=3, 4, 15 Hz, 1H, CH equatorial), 2.85 (ddd, J=5, 12, 12 Hz, 1H, C HCOOCH$_2$), 2.6 (m, 1H, CHCH$_2$NO$_2$), 2.4 (ddd, J=3, 5, 15 Hz, 1H, CH equatorial), 1.8 (m, 2H, CH axials), 1.6 (s, 3H, CH$_3$), 1.4 (s, 3H, CH$_3$), 0.16 (s, 9H, Si(CH$_3$)$_3$).

$^{13}$C NMR (CDCl$_3$): delta values 173.6, 106.3, 97.9, 88.5, 75.2, 66.3, 65.4, 52.0, 41.8, 41.5, 38.7, 33.0, 31.4, 30.3, 0.3.

HRMS, m/e (relative intensity): 354.1366 [M-CH$_3$]$^+$ (11.3), 294.1158 [M-OC$_3$H$_6$]$^+$ (5.4), 264.1184 [294-NO$_2$]$^+$ (46.5), 73.0472 [TMSi]$^+$ (100); calcd for C$_{16}$H$_{24}$N O$_6$Si 354.1373.

Example 9

Oxidation of 1-hydroxy-5-methoxy-naphthalene to 1,4-dihydro-4,4,5-trimethoxy-1-oxonaphthalene by Iodobenzene Diacetate A solution of 15.5 g (48 mmol) of iodobenzene diacetate and 22 g of NaHCO$_3$ in 100 mL of methanol/trimethyl orthoformate (1/1) was stirred at room temperature for 30 minutes. To this mixture a solution of 3.74 g of 1-hydroxy-5-methoxynaphthalene (21.5 mmol) in 250 mL of methanol was added dropwise. The color of the mixture changed from orange to greenish yellow over 2 hours at room temperature.

Ether (150 mL) was added to the mixture, and then sat. NaHCO$_3$ (75 mL). The aqueous washings were back extracted with ether (75 mL×3). The combined ethereal extracts were washed with saturated aqueous sodium chloride solution and dried over sodium sulfate. The solution was evaporated to give 1,4-dihydro-4,4,5-trimethoxy-1-oxonaphthalene.

Flash chromatography of this product with elation using EtOAc:Hex 1:1 yielded 3.70 g (74 percent) of crystals of 1,4-dihydro-4,4,5-trimethoxy-1-oxonaphthalene, mp 62–63 degrees centigrade.

$^1$H NMR (CDCl$_3$): delta values 7.7 (d, 1H, aromatic), 7.52 (t, 1H, aromatic), 7.16 (d, 1H, aromatic), 6.80 (m, 2H, HC=CH), 3.92 (s, 3H,OCH$_3$), 3.14 (s, 6H, (OCH$_3$)$_2$) (2OCH$_3$).

UV (MeOH): maximum wavelength: 222 nm.

IR (neat): 1672, 1635, 1589, 1580, 1300, 1178, 1068, 1031 cm$^{-1}$.

Example 10

3-[(2beta-Carbomethoxy-4beta-ethynyl-4alpha-6alpha-(di-O-isopropylidenyl)-cyclohexanyl-1-yl)]-nitromethyl-4,4,5-trimethoxy-1-oxo-1,2,3,4tetrahydronaphthalene A solution of 0.904 g (3.0 mmol) of trans nitroacetonide (acetonide of methyl 3alpha,5alpha-dihydroxy-5beta-(trimethylsilylethynyl)-2alpha-nitromethylcyclohexane-1betacarboxylate), 1.34 g (5.7 mmol) of 1.4-dihydro-4,4,5-trimethoxy-1-oxonaphthalene and 750 microL (5 mmol) of DBU in 0.5 mL of acetonitrile was stirred for 5 days at room temperature. Methylene chloride (5 mL) was added to the mixture and the solution was chromatographed on a column packed with 150 g of silica gel (5 cm column, 30:70 v/v ethyl acetate/hexanes slurry). The material on the column was eluted with 400 mL of 30:70 v/v ethyl acetate/hexanes. After the nitro acetonide was eluted, as followed by TLC (iodine development), the chromatographic separation was continued with 1000 mL of 50:50 v/v ethyl acetate/hexanes.

Evaporation of the solvent from the various fractions gave recovered nitro acetonide (0.66 g, 2.2 mmol), recovered dimethyl ketal (1.03 g, 4.4 mmol) and product, 3-[(2beta-carbomethoxy-4beta-etnyny-4alpha,6alpha-(di-O-isopropylidenyl)-cylohexanyl-1-yl)-nitromethyl]-4,4,5-trimethoxy-1-oxo-1,2,3,4-tetrahydronaphthalene (0.274 g, 0.51 mmol, 62 percent based on recovered acetonide) as an oily mixture of diasteromers.

IR (ATR thin film): 1733 (COOMe), 1686 (C=O), 1588, 1579 ($NO_2$) cm$^{-1}$.

$^1$H NMR (CDCl$_3$): delta values 7.6 (d, 1H, Ar), 7.4 (dd, 1H, Ar), 7.1 (d, 1H, Ar), 5.3–5.0 (d, 1H, CHNO$_2$), 4.4–4.0 (m, 1H, CHOC), 3.7 (s, 3H, ArOCH$_3$), 3.5 (s, 3H, COOCH$_3$), 3.3–2.8 (complex group of overlapping protons, 10H), including (COCH$_3$ ketal, 3.2, 3H, and 3.1, 3H), (O=CCH2, 2H), and (CHCOOCH$_3$, 1H), (HCCHNO$_2$, 1H)), 2.5 (s, 1H, C≡CH), 2.5 (d, 1H, CH$_2$), 2.2 (d, 1H, CH$_2$), 1.8 (d, 1H, NO$_2$CHCH), 1.6–1.5 (m, 2H, CH$_2$, 1.5 (s, 3H, CCH$_3$), 1.2 (s, 3H, CCH$_3$).

$^{13}$C NMR (CDCl$_3$): mixture of two diastereomers, (195.4, 195.1), (174.3, 173.2), (157.6, 157.5), (134.3, 134.0), (130.3, 130.2), (125.3), (120.05, 120.0), (117.2, 117.15), (101.6, 101.6), (97.9, 97.7), (86.1, 85.10), (84.48, 84.42), (72.6, 72.5), (66.0, 65.9) (64.5, 64.4), (55.9), (52.2, 51.6), (50.56, 50.46), (50.4, 50.1), (43.4 43.1), (42.8, 42.7), (42.0, 40.7), (39.77, 39.70), (35.8, 35.6), (32.7, 32.6), (31.2, 31.1), (30.05, 29.9).

Example 11

9beta-Ethynyl-5,5-dimethoxy-12-hydroxy-7alpha,9alpha-di-(O-isopropylidenyl)-4-methoxy-6-nitro-5,5a,6,6a,7,8,9,10,10a-decahydro-11-naphthacenone Sodium hydride (24 mg, 0.8 mmol) was added in one portion to a solution of 3-[(2beta-carbomethoxy-4beta-ethynyl-4alpha,6alpha-(di-O-isopropylidenyl)-cyclohexanyl-1-yl)]-nitromethyl-4,4,5-trimethoxy-1-oxo-1,2,3,4-tetrahydronaphthalene (0.380 g, 0.72 mml) and methanol (3 drops) in 25 mL of toluene at 0 degrees centigrade. After 15 minutes' stirring, the cooling bath was removed. The reaction mixture was stirred for an additional 18 hours at room temperature and then washed briefly with 10 mL of cold 5 percent HCl. The organic phase was further washed with 5 mL of saturated aqueous sodium bicarbonate solution, with two 10-mL portions of saturated aqueous sodium chloride solution and dried over sodium sulfate. The solvent was evaporated to give 0.260 g of crude oily product, which was recrysallized from toluene to yield 0.252 g (0.42 mmol, 71.0 percent) of 9beta-ethynyl-5,5-dimethoxy-12-hydroxy-7alpha,9alpha-(di-O-isopropylidenYl)-4-methoxy-6-nitro-5,5a,6,6a,7,8,9,10,10a,11-decahydro-11-naphthacenone, white crystalline solid, mp 234 degrees centigrade (decomp).

IR (ATR thin film): 3320 (C=C—OH), 2260 (C≡CH), 1559 ($NO_2$) cm$^{-1}$.

$^1$H NMR (CDCl$_3$): delta values 16.2 (s, 1H, C=COH), 7.8 (d, 1H, ArH), 7.6 (t, 1H, ArH) 7.1 (d, 1H, ArH), 5.2 (dd, J=1, 3 Hz, 1H, CHNO$_2$), 4.6 (d, J=4.5 Hz, 1H, CHOC), 3.9 (s, 3H, ArOCH$_3$), 3.9 (ddd, J=4.5, 13, 13 Hz, 1H, O=CCH), 3.5 (d, J=4.5 Hz, 1H, C=C—CHCHNO$_2$), 3.4 (s, 3H, OCH$_3$ ketal), 3.1 (ddd, 1H, CH$_2$ equatorial), 3.0 (s, 3H, OCH$_3$ ketal), 2.9 (ddd, J=3, 3, 13 Hz, 1H, CH$_2$ equatorial), 2.5 (s, 1H, C≡CH), 1.8 (d, J=12 Hz, 1H, NO$_2$CHCHCO), 1.67 (d, 1H, CH$_2$ axial), 1.64 (s, 3H, OCCH$_3$), 1.5 (dd, J=12, 12 Hz, 1H, CH$_2$ axial), 1.3 (s, 3H, OCCH$_3$).

$^{13}$C NMR (CDCl$_3$): HETCOR-DEPT 196.9 (C=O), 172.6 (ArC=COH), 157.2 (ArC JCOH), 133.0 (Ar), 130.6 (ArH), 122.8 (Ar), 119.4 (ArH), 115.7 (ArH), 101.6, 101.3, 98.4, 85.2 (C≡CH), 79.9, 72.1 (CHNO$_2$), 69.5 (CHOC), 66.3, 55.8 (ArOCH$_3$), 52.5 (COCH$_3$), 51.4 (COCH$_3$), 46.0 (NO$_2$CCHCO), 44.8 (CHCNO$_2$), 40.2 (CH$_2$), 35.3 (CHC=O), 34.3 (CH$_2$), 30.8 (OCCH$_3$), 30.4 (OCCH$_3$).

UV-Vis: maximum wavelengths 350 (11200), 344 (11900) 341(12300), 232(10678).

Example 12

9beta-Acetyl-7alpha,9alpha,12-trihydroxy-4,5-dimethoxy-6-nitro-6,6a,7,8,9,10,10a,11-octahydro-11-naphthacenone Sulfuric acid (1.5 mL, 3M) was added to a solution of 212 mg (0.42 mmol) of 9beta-ethynyl-5,5-dimethoxy-12-hydroxy-7alpha,9alpha-(di-O-isopropylidenyl)-4-methoxy-6-nitro-5,5a,6,6a,7,8,9, 10,10a,11-decahydro-11-naphthacenone in 20 mL of THF. The solution immediately turned a bright yellow color. To the resulting solution was added 24.5 mg (0.11 mmol) of HgO. The resulting mixture was stirred for 4 hours at room temperature, cooled to 0 degrees centigrade and neutralized to pH 6 with 0.5 g of potassium hydroxide in 3 mL of water. The mixture was poured into 20 mL of water and extracted with four 20-mL portions of ethyl acetate. The combined organic layers were washed with two 20-mL portions of water and with 20 mL of saturated aqueous sodium chloride solution and dried over sodium sulfate. The solvent was removed by evaporation to yield 0.176 g (0.39 mmol, 93.2 percent) of 9beta-acetyl-7alpha,9alpha,12-trihydroxy-4,5-dimethoxy-6-nitro-6,6a,7,8,9,10,10a, 11-octahydro-11-naphthacenone, yellow solid. Product recrystallized from acetone gave fine yellow needle crystals, mp 186 degrees centigrade (decomp).

IR (ATR thin film): 3427 (OH), 1711 (C=O), 1628, 1591, 1554 ($NO_2$) cm$^1$.

$^1$H NMR (THF D$_4$): delta values 14.3 (s, 0.5H, ArOH), 8.0 (d, 1H, ArH), 7.5 (dd, 1H, ArH), 7.2 (d, 1H, ArH),m 6.4 (d, 1H, CHNO$_2$), 5.5 (bs, 0.5H, OH), 5.0 (bs, 0.5H, OH), 4.6 (m, 1H, CHOH), 3.9 (s, 2H, ArOCH$_3$ D-ring), 3.7 (s, 3H, ArOCH$_3$ C-ring), 3.7 (ddd, 1H, COCH), 2.6 (ddd, 1H, CH$_2$ equatorial), 2.5 (ddd, 1H, CH$_2$ equatorial), 2.3 (s, 3H, COCH$_3$), 1.8 (m, 1H, NO$_2$CHCH), 1.8–1.7 (m, 2H, CH$_2$ axials partly obscured by THF peak).

$^{13}$C NMR (THF D$_4$): delta values 211.3 (C=O), 206.7 (C=O), 160.0, 157.3, 128.5, 122.4, 117.6, 117.5, 112.5, 112.4, 110.1, 81.9, 80.4, 69.87, 69.83, 62.7, 56.6, 46.0, 39.1, 36.2, 35.9, 35.8.

UV-Vis (MeOH) maximum wavelengths: 339, 321, 262, 220 nm.

Example 13

9beta-Acetyl-7alpha,9alpha-dihydroxy-4-methoxy-6-nitro-5,6,6a,7,8,9,10,10a,11,12-decahydro-5,11-12-naphthacenetrione Thallium nitrate (55 mg, 0.11 mmol) was added to a solution 50 mg (;0.11 mmol) of 9beta-acetyl-7alpha,9alpha,12-trihydroxy-4,5-dimethoxy-6-nitro-6,6a,7,8,9,10,10a,11-octahydro-11-naphthacenone in 5 mL of acetone at 0 degrees centigrade. The mixture was brought to room temperature and stirred for 2 hours. Additional thallium trinitrate (11 mg, 0.02 mmol) was added and stirring was continued for 1 hour. The resulting solution was poured into 20 mL of water and extracted with three 25-mL portions of ethyl acetate. The combined organic extracts were washed with two 25 mL portions of water and with 25 mL of saturated aqueous sodium chloride solution and dried over sodium sulfate. The solvent was evaporated to yield 99.5 mg of crude yellow product, an orange solid.

The product, which turned black upon standing, was dissolved in 5 mL of 9:1 ethyl acetate/hexanes v/v. After 16 hours, an orange precipitate had formed. The supernatant was removed by decantation and the resulting solids dried to give 25 mg (0.06 mmol, 54.5 percent) of 9beta-acetyl-7alpha,9alpha-dihydroxy-4-methoxy-6-nitro-5,6,6a,7,8,9,10,10a,11,-12-decahydro-5,11,12-naphthacenetrione, mp 242 degrees centigrade (decomp).

$^1$H NMR (acetone D$_6$): delta values 7.9 (dd, 1H, aromatic), 7.7 (d, 1H, aromatic), 7.6 (d, 1H, aromatic), 6.2 (d, J=4.5 Hz, 1H, CHNO$_2$), 5.5 (s, 0.5, OH), 4.9 (m, 0.5, OH), 4.7 (m. 1H, C$\underline{H}$OH), 4.0 (s, 3H, ArOCH$_3$), 3.5 (ddd, J=4, 12, 13, Hz, 1H, COCHC$\underline{H}_2$), 2.8 (ddd, J=1, 5, 13 Hz, 1H, COC $\underline{H}$C$\underline{H}_2$ equatorial), 2.4 (ddd, 1H, COHC$\underline{H}_2$ equatorial), 2.3 (s, 3H, COCH$_3$), 1.9 (m, 1H, NO$_2$ CHC$\underline{H}$ partially obscured by acetone quintet).

IR (ATR thin film): 1709 (C=O), 1663, 1665, 1587, 1560 (NO$_2$) cm$^{-1}$.

UV-Vis (MeOH) maximum wavelengths: 424 nm 274, 258 nm.

EXAMPLE 14

7alpha,9alpha-(Di-O-isopropylidenyl)-4,5-dimethoxy-9beta-ethynyl-12-hydroxy-6-nitro-6,6a,7,8,9,10,10a,11-octahydro-11-naphthacenone A catalytic amount of pyridinium tosylate (5 mg) was added to a solution of 100 mg (0–20 mmol) of the decahydro-11-naphthacenone (example 11) in 20 mL of CH$_2$Cl$_2$. The mixture was refluxed for 6 hours while the color of the solution changed from light to shiny yellow. The reaction mixture was washed with water (2×20 mL) dried over Na$_2$SO$_4$ and the solvent was removed in vacuo. The yellow residue was recrystallized from hexane: ethyl acetate (9:1) to give the octahydro-11-naphthacenone as a mixture of 2 stereoisomers at C$_6$ (88 mg, yield 94 percent). The isomer can be separated by chromatography. Major isomer 85 percent m.p. 243–244 degrees centigrade.

IR (KBr) 3262, 1733, 1616, 1572, 1563, 1554, 1501, 1456, 1430, 1382, 1276, 1261, 1215 cm$^{-1}$.

NMR (360 MHz, CDCl$_3$): major isomer 14.01(s, 1H), 8.12(d, 1H), 7.49(t, 1H), 7.02(d, 1H), 6.35(d, J=4 H$_2$1H), 4.73(d, 1H), 3.95(s, 3H), 3.27(m, 1H), 2.16(d, 1H), 1.61(s, 3H), 1.30(s, 3H), ppm.; (minor isomer 15 percent) 13.34(s, 1H), 8.05(d, 1H), 7.47(t, 1H), 7.05(d, 1H), 6.21(d, J=10.4 H$_2$1H), 4.40(d, 1H), 3.91(s, 3H), 3.71(s, 3H), 3.66(d, 1H), 3.12(m, 2H), 2.53(s, 1H), 2.19(m, 2H), 1.67(s, 3H), 1.37 (s, 3H) ppm.

UV Vis. (MeOH) maximum wavelength: 230, 266, 328, 396 nm.

Anal. Calcd. for C$_{25}$H$_{25}$O$_8$N: C, 64.2, H, 5.39, N, 3.00. Found: C, 64.9, H, 5.31, N: 3.04.

EXAMPLE 15

7alpha-9alpha-(Di-O-isopropylidenyl)-9beta-ethynyl-11-hydroxy-4-methoxy-6-nitro7,8,9,10-tetrahydro-5,12-nathacenedione A solution of 36 mg (0.075 mmol) of the octahydro-11-naphthacenone and 60 mg (0.675 mmol) of NaHCO$_3$ in 10 mL of acetone was treated with a solution of 167 mg (3 mmol) of cerium ammonium nitrate (CAN) and 1 mg of dichlorodicyanobenzoquinone (DDQ) in 2 mL of acetone added in one portion at 0 degrees centigrade. The reaction mixture was stirred at room temperature for 1.5 hours during which the color changed from shiny yellow to orange red, and then 25 mL of CH$_2$Cl$_2$ was added. The mixture was filtered through over Celite. The organic layer was washed with saturated NaCl solution (2×20 mL), dried over Na$_2$SO$_4$, and evaporated to give the tetrahydro-5,12-naphthacenedione as a red crystals (29 mg, 86 percent). mp greater than 258 degrees centigrade (decomp).

IR (KBr) 3306, 1620, 1588, 1529, 1491, 1369 cm$^{-1}$.

$^1$H NMR (360 MHz, CD$_2$Cl$_2$ 15.00(s, 1H), 7.19 (d, 1H) 7.57(t, 1H), 7.36(d, 1H), 4.50(m, 1H), 4.00(s, 3H), 3.12(m, 2H), 2.65(m, 2H), 2.57(s, 1H), 1.68(s, 3H), 1.37(s, 3H) ppm.

UV-Vis. (MeOH) maximum wavelength: 223, 240, 248, 358, 440 nm; (CHCl$_3$) 246, 370, 390, 416, 436 nm.

Example 16

6-Desoxy-6-nitrodaunomycinone

A solution of 12 mg of (0.027 mmol) of the tetrahydro-5,12,-naphthacenedione in 2.5 mL of tetrahydrofuran was treated with 150 microL of H$_2$SO$_4$(3M) and then 5 mg of mercuric oxide at 0 degrees centigrade and stirred at room temperature for 24 hours. The turbid solution was neutralized with NaHCO$_3$ to pH 8, and extracted with CH$_2$Cl$_2$ (10×) 15 mL). The extract was dried over Na$_2$SO$_4$, and evaporated to yield 6-desoxy-6-nitrodaunomycinone as a red solid (7 mg, 61.4 percent). Flash chromatography on silica (60–200 mesh) eluting with 70:25:5(ethyl acetate:hexane:MeOH) afforded 2 mg of the pure mycinone as red crystals.

IR (CHCl$_3$), 3364, 1708, 1662, 1615, 1591, 1525, 1499, 1446, 1278, 1336 cm$^{-1}$.

$^1$H NMR (360) MHz, CD$_2$Cl$_2$ 15.15(s, 1H), 8.06 (d, 1H), 7.82(t, 1H), 7.42(d, 1H), 5.44(m, 1H, OH), 4.61(s, 1H), 4.09(s, 3H), 3.79(m, 1H, OH), 3.21(d, 1H), 3.00(d, 1H), 2.40(s, 3H), 2.30(d, 1H), 2.21(m, 1H ) ppm.

UVVisi maximum wavelengths: (CHCl$_3$) 245, 250, 420, 446 nm; (MeOH) 360, 385, 418, 441, 466 nm.

Example 17

6-Amino-9beta-ethynyl-4-methoxy-7alpha,9alpha,11-trihydroxy-7,8,9,10-tetrahydro-5,12-naphthacenedione A solution of 15 mg (0.033 mmol) of the tetrahydro-5,12-naphthacenedione from example 15 and 96 mg (0.70 mmol) of NaOOCCH$_3$;3H$_2$O in 2 mL of CH$_3$OH was treated with SnCl$_2$H$_2$O (183 mg, 0.88 mmol), in 3 portions over a 90 min. at room temperature. During the addition the color of the solution changed to yellow. After the SnCl$_2$ was added, the mixture was stirred for 1 h, and the solvent was evaporated. A mixture of 15 mL of CH$_2$Cl$_2$ and 15 mL of saturated aqueous NaHCO$_3$ was added and the mixture was stirred for 30 min. During the stirring the color changed to pink and CO$_2$ was evolved.

The mixture was filled through Celite and extracted with CH$_2$Cl$_2$(3×20 mL). The combined organic layers were washed with saturated aqueous NaCl, dried (Na$_2$SO$_4$), and evaporated to yield 14 mg of yellow solid. TLC showed that this was a mixture of 2 compounds. Flash chromatography using elution with hexane: ethyl acetate: MeOH (75:20:5) gave two compounds, the 6-desoxy-6-nitro starting material (6mg), and 6-amino-9beta-ethynyl-4-methoxy-5,7alpha,9alpha,11,12-pentahydroxy-7,8,9,10-tetrahydronaphthacene (7.5 mg) as shining yellow crystals (mp, 234–238 degrees centigrade). NMR: 14.1(s, 1H,OH)O),13.4(s,2H,OH),8.1(d, 1H), 7.7(t,1H),7.2(d,1H),5.0(m, 1H),4.25(m, 1H,OH), 4.04(s, H),3.62(m,2H,NH$_2$),3.15(m1H,OH),2.95(q,2H), 2.55(s, H,C≡CH),1.96(m,2H).ppm.

FT-IR (KBr) 3647, 3375,3289, 1671, 1634, 1601, 1582 cm$^{-1}$.

UV-Vis (CHCl$_3$) maximum wavelengths 446,422,274, 250 nm. A saturated solution of 17.5 mg (0.032 mmol ) ceric ammonium nitrate in acetone was added at 0 degrees centigrade to pentahydroxynaphthacene (7mg, 0.016 mmol) and NaHCO$_3$(10 mg) in 2 mL of acetone. The reaction mixture was stirred for 5 h at room temperature and then filtered through Celite and extracted with CH$_2$Cl$_2$ (7×10 mL). Evaporation yielded mg of the amino trihydroxy-5,12-naphthacenone as purple red crystals.

$^1$H NMR (CD$_2$Cl$_2$), 14.80(s,1H,OH), 8.10 (d,1H), 7.85(t, 1H),7.42(d,1H),5.35(d,1H),4.30(d,1H,OH), 4.09 (s,3H), 3.57 (m,2H),3.35(m,1H,OH),3.15(m,2H),2.55(s, 1H), 1.95(m,2H)ppm.

UV-Vis (CHCL$_3$ ) maximum wavelength: 498, 442, 313, 269 nm.

FT-IR(KBr) 3644, 3277, 1671, 1631, 1580 cm$^{-1}$.

Example 18

Daunomycinone

A solution of 7 mg (0.018 mmol) of the amino-5,12-naphthacenedione and 1 mg of pyridinium tosylate in 2 mL of dimethoxyethane was treated with 15 microL of isoamylnitrite. As the mixture was stirred at room temperature a purple precipitate formed, and 0.5 mL of 0.01N HCL was added; after stirring had been continued for 5 h, the visible spectrum of the mixture showed absorption at 515 nm. Then HgO (40 mg, 0.18 mmol), was added and stirring was continued for 24 h. The mixture was filtered through Celite, extracted with CH$_2$Cl$_2$ (15×10 mL) and evaporated to yield 10 mg of red solid. Flash chromatography with elution with ethyl acetate:hexane:MeOH((90:5:5), followed by recrystalization from CHCl$_3$ gave 3 mg of daunomycinone (mp 217–221 degrees centigrade).

$^1$H-NMR (CD$_2$Cl$_2$, 360 MHz), 14.22 (s, 1H), 13.47(2, 1H), 8.21(d,1H), 8.00 (t,1H), 7.61 (d,1H), 5.48 (m,1H), 4.23 (s,3H), 4.07 (s,3H), 3.95 (d, 1H), 3.10 (m,2H), 2.57 (s,3H), 2.30 (m,2H) ppm.

FT-IR (CH$_2$Cl$_2$) 3540, 3053, 2927, 1712, 1616, 1578, 1420 cm$^{31\ 1}$.

UV-Visi (MeOH) maximum wavelength: 532, 495, 476, 287, 253, 234nm.

Example 19

4,5-dimethoxy-7alpha,9alpha-(di-O-isopropylidenyl)-9beta-ethynyl-12-hydroxy-11-imino-6-nitro-6,6a,7,8,9,10,10a,11-octahydronaphthacene, The nitrooctahydro-11-naphthacenone (10 mg, 0.021 mmol) was added to 25 mL of methanol which had been saturated with ammonia at 0 degrees C. The reaction mixture was stirred at room temperature with continued bubbling of NH$_3$ for 2 h (hours). The flow of ammonia was stopped; the reaction flask was sealed and stirring was continued at room temperature for 24 h. The color of the solution changed from yellow to brown. The reaction mixture was evaporated and the residue was flash chromatographed (60–200 mesh silica). Elution with ethyl acetate:hexane (25:75) gave 4,5-dimethoxy-7alpha,9alpha-(di-O-isopropylidenyl)-9beta-ethynyl-12-hydroxy-11-imino-6-nitro-6,6a,7,8,9,10,10a,11-octahydronaphthacene, as yellow needles (9 mg, 0.018 mmol, 90 percent), m.p: 236–237 degrees C. (210 degrees C., dec.); $^1$H NMR (500 MHz, CDCl$_3$, ppm), 14.6 (b, 1H, Ar—OH), 8.2 (d, 1H, Ar—H), 7.4 (t, 1H, Ar—H), 7.1 (d, 1H, Ar—H) 6.9 (s, b, 1H, NH), 6.3 (d, J=3.2 Hz, 1H, H—CNO$_2$), 4.7 (d, J=4.5 Hz, 1H, H$_7$ ), 4.0 (m, 1H, H$_{10a}$), 3.96 (s, 3H, OCH$_3$). 3.7 (s, 3H, OCH$_3$), 3.1 (dt, J$_{gem}$=14.8 Hz, J$_{H7-H8e}$=4.5 Hz, 1H, H$_{8e}$), 2.7 (dt, J$_{gem}$=14.8 Hz, J$_{H7-H10e}$=12.8 Hz), 2.6 (s, 1H, C≡CH), 2.0 (dd, J$_{6a-10a}$=12.3 Hz, J$_{6a-6}$=3.2 Hz, 1H, H$_{6a}$), 1.7 (q, 2H, H$_{10ax}$, H$_{8a}$), 1.66 (s, 3H, CH$_3$), 1.3 (s, 3H, CH$_3$); $^{13}$C NMR (125 MHz, CDCl$_3$, ppm), 176.3, 171.5, 156.0, 142,8, 134.9, 127.2, 122.5, 119.5, 118.5, 113.0, 103.3, 98.6, 84.9, 81.7, 72.7, 68.6, 66.0, 61.7, 56.5, 46.0, 40.8, 34.2, 30.6, 30.5; FT-IR (KBr neat, cm$^{-1}$), 3419, 3284, 2964, 2160, 1554, 1539, 1467; UV-Vis (CH$_3$OH, nm) 224 (15779), 273 (16300), 328 (3291), 428 (7854), 448 (7168); FAB-MS: 467 (M+1,45), 420 (100), 307 (15), 154 (100, 136 (85).

Example 20

11-amino-7alpha,9alpha-(di-O-isopropylidenyl)-9beta-ethynyl-4-methoxy-6-nitro-7,8,9,10-tetrahydro-5,12-naphthacenedione Cerium ammonium nitrate (18 mg, 0.035 mmol) and a catalytic amount of dichlorodicyanobenzoquinone (DDQ, 0.1 mg) and 20 mg of NaHCO$_3$ were added to the nitroiminonaphthacene (4 mg; 0.0086 mmol) in 1 mL wet THF solution. The reaction mixture was stirred at room temperature for four hours until TLC indicated that all of the starting material had reacted. The color of the solution had changed from deep yellow to red. The reaction mixture was filtered, and the solvent was evaporated. Flash chromatography of the residue involving elution with ethyl acetate-hexane (25:75) yielded 11-amino-7alpha,9alpha-(di-O-isopropylidenyl)-9beta-ethynyl-4-methoxy-6-nitro-7,8,9,10-tetrahydro-5,12naphthacenedione (3.4 mg, 0.0076 mmol, 89 percent) reddish needles: m.p. 242–244 degrees C. (dec.); 1H NMR (500 MHz, CDCl$_3$, ppm), 8.0 (d, 1H, Ar—H), 7.7 (t, 1H, Ar—H), 7.3 (d, 1H, Ar—H), 6.9 (b, 2H, NH$_2$), 5.0 (t, J=2.82 Hz, 1H, H—C—O), 4.0 (s, 3H, OCH$_3$), 3.1 (dd, 1H, J$_{gem}$=16.9 Hz, H$_{10e}$), 3.0 (dt, 1H, J$_{gem}$=16.5 Hz, J$_{8e-7}$=2.82 Hz, H$_{8e}$), 2.7 (d, 1H, H$_{10a}$, J$_{gem}$=16.9 Hz), 2.65 (s, 1H C≡CH), 2.1 (dd, 1H, J$_{gem}$=16.9Hz, H$_{8a}$), 1.6 (s, 3H, CH$_3$), 1.1 (s, 3H, CH$_3$); $^{13}$C NMR (125 MHz, acetone-d$_6$, ppm), 181.0, 179.1, 148.3, 143.0, 136.5, 133.9, 133.7, 123.6, 118.5, 117.2, 116.4, 111.7, 98.1, 85.1, 71.6, 67.0, 64.2, 55.7, 39.4, 32.4, 30.4, 29.2, 28.9, 28.8; FT-IR (KBr neat, cm$^{-1}$), 3440, 3301, 2987, 2929, 2854, 2160, 1660, 1635, 1583, 1540, 1467; UV-Vis (CH$_3$OH, nm), 230 (11872), 372 (1314), 382 (1316), 474 (2666). The same product was obtained in 90 percent yield by refluxing the nitroiminonaphthancene in O$_2$/DMF overnight. Chromatography was not needed.

Example 21

11-amino-6,11-didesoxy-6-nitrodaunomycinone

A solution of 10 mg (0.025 mmol) nitroaminonaphthacenedinoe in THF (2 mL) was treated with mercuric oxide (30 mg) and 1 mL of 1N H$_2$SO$_4$. The reaction mixture was stirred at room termperature for 24 hours and then acidified to pH 1. The reaction mixture was extracted with ethyl acetate (3×20 mL). The combined organic layers were washed with saturated aqueous sodium chloride (30 mL) and dried over anhydrous sodium sulfate. The solvent was evaporated to give 10 mg crude product. Flash chromatograPhY using 50 percent ethyl acetate and hexane as elutent gave 5 mg (55 percent) of 11-amino-6,11-didesoxy-6-nitrodaunomycinone as an orange solid; m.p. 274–275 degrees; $^1$H NMR (500 MHz, DMSO-d$_6$, ppm), 7.92 (d, 1H, Ar—H), 7.85 (t, 1H, Ar—H), 7.60 (s, 2H, NH$_2$), 7.55 (d, 1H, Ar—H), 6.00 (s, 1H, OH), 5.60 (d, 1H, OH), 4.6 (m, 1H, H$_7$), 4.0 (s, 3H, OCH$_3$), 3.0 (d, 1H, H$_{10e}$), 2.6 (d, 1H, H$_{10a}$), 2.4 (dd, 1H, H$_{8e}$), 2.35 (s, 3H, CH$_3$), 2.0 (dd, H, H$_{8a}$); $^{13}$C NMR (125 MHz, dmso-D$_6$, ppm), 211.1, 183.7, 181.5, 159.6, 149.6, 145.4, 23.9; 135.0, 132.8, 125.4, 120.8, 118.6, 117.7, 115.0, 110.0, 76.4, 65.8, 56.3, 40.0, 33.5, 23.9; FT-IR (KBr, cm$^{-1}$), 3442, 3309, 1715, 1636, 1616, 1581, 1531; UV-Vis (CH$_3$OH, nm), 471, 430, 253, 221.

Example 22

6,11-diamino-7alpha,9alpha-(di-O-isopropylidenyl)-9beta-ethynyl-4-methoxy-7,8,9,10-tetrahydro-5,12-naphthacenedione A solution of 41 mg (0.091 mmol) of the nitroaminonaphthacenedione in methanol (5 mL) was treated with sodium acetate (120 mg, 0.9 mmol) and then stannous chloride (167 mg, 0.9 mmol) which was added in three portions over a period of 90 minutes at room temperature under a nitrogen atmosphere. After the mixture had been stirred overnight, its color had changed from orange to purple. Then 100 mL of CH$_2$Cl$_2$ and 10 mL of saturated aqueous sodium bicarbonate were added. The mixture was stirred at room temperature for one hour and filtered through Celite. The filtrate was washed with saturated aqueous sodium chloride (2×20 mL), and then dried over anhydrous sodium sulfate. The mixture was separated by chromatography (60–200 mesh silica treated with triethylamine and dried at 200 degrees C. for 12 h). Elution with hexane:ethyl acetate (50:50) gave 11 mg of a pink solid and 28 mg of the starting compound. The pink solid was treated with silver oxide (148 mg 0.64 mmol) in 2 mL of ethanol for two hours. The solution was filtered and the filtrate was evaporated to yield a purple solid, purified by chromatography on the basic silica gel. Elution with hexane:ethyl acetate (50:50) yielded 6,11-diamino-7alpha,9alpha-(di-O-isopropylidenyl)-9beta-ethyl-4-methoxy-7,8,9,10-tetrahydro-5,12-naphthacenedione, 8 mg (66 percent based on the recovered starting nitroaminonaphthacenedione): mp:206–208 degrees C. (dec); FT-IR (KBr, cm$^{-1}$), 3442, 3309, 3268, 1637, 1616, 1600, 1581; UV-Vis (CH$_3$OH, nm), 229 (17338), 249 (14415), 540 (4700); $^1$H NMR (500 MHz, CDCl$_3$, ppm), 8.0 (d, 1Gm, Ar—H), 7.7 (t, 1H, Ar—H), 7.5 (d, 1H, Ar—H), 7.2 (s, 4H, NH$_2$), 5.0 (t, 1H, H$_7$), 4.0 (s, 3H, OCH$_3$), 3.5 (d, 1H, H$_{10e}$), 2.9 (dt, 1H, H$_{8e}$), 2.8 (d, 1H, H$_{10a}$), 2.6 (s, 1H, C≡CH, h$_{8a}$), 1.99 (d, 1H), 1.6 (s, 3H, CH$_3$), 1.1 (s, 3H, CH$_3$).

Example 23

6,11-diamino-6,11-didesoxydaunomycinone

A solution of the diaminonaphthacendione (8 mg, 0.019 mmol) in 1 mL of THF was stirred at room temperature under a nitrogen atmosphere and 50 mg (0.23 mmol) of HgO and two drops of 2N HCl were added. The reaction mixture was stirred at room temperature under nitrogen atmosphere overnight and filtered through Celite. The filtrate was evaporated and the residue was purified by chromatography on basic silica (60–200 mesh). Elution with ethyl acetate : hexane (70:30) gave 6,11-diaminodaunomycinone 3.5 mg (47 percent) as blue solid: $^1$H NMR (500 MHz, CDCl$_3$, ppm), 8.1 (d, 1H, Ar—H), 7.8 (t, 1H, Ar—H), 7.4 (d, 1H, Ar—H), 7.2 (s, 4H, NH$_2$), 5.2 (t, 1H, H$_7$), 4.0 (s, 3H, OCH$_3$), 3.5 (b, 2H, OH), 3.2 (d, 1H, H$_{10e}$), 2.9 (d, 1H, H$_{10a}$), 2.4 (s, 3H, CH$_3$), 2.3 (d, 2H, H$_{8e}$); FT-IR (KBr, cm$^{-1}$), 3417, 1710, 1652, 1617, 1602; UV-Vis (MeOH), 228, 249, 542.

Example 24

11-fluoro-6,11-didesoxy-6-nitrodaunomycinone

Hexafluorophosphoric acid (17 microliters, 60 percent in H$_2$O, 0.07 mmol) was added at room temperature to a solution of 11-amino-6,11-didesoxy-6-nitrodaunomycinone (5 mg, 0.012 mmol) and THF (1 mL) in a waxed flask. The reaction mixture was stirred at room temperature for 10 min, then cooled to zero degrees Centigrade, and i-C$_5$H$_{11}$ONO (19.32 mg, 0.07 mmol) was added. The solution was stirred at zero degrees Centigrade for an additional 15 minutes and a reddish solid was formed. The reddish solid was collected, dried on filter papers and dissolved in triethylamine trihydrofluoride (1 mL). The mixture was irradiated with ultrasound at 40 degrees Centrigrade for two hours. Ethyl acetate (10 mL) was added. The organic layer was washed with water (2×5 mL) and dried (MgSO$_4$). TLC showed that there was only one spot (R$_f$=0.45, 30/70 hexane/EtOAc). The solvent was evaporated to give 11-fluoro-6,11-didesoxy-6-nitrodaunomycinone (5 mg, 91 percent) as an orange yellow solid: $^1$H NMR (500 MHz, CDCl$_3$) Delta: 8.0 (d, 1H, Ar—H), 7.8 (t, 1H, Ar—H), 7.4 (d, 1H, At—H), 5.2 (t, 1H, C$_7$H), 4.9 (bs, 1H, OH), 4.1 (bs, 1H, OH), 4.0 (s, 3H, OCH$_3$), 3.2 (dd, 1H, C$_{10}$H$_e$), 3.1 (dd, 1H, C$_8$H$_e$), 2.5 (s, 3H, CH$_3$), 2.4 (dd, 1H, C$_{10}$H$_a$), 2.1 (d, 1H, C$_8$H$_a$); $^{19}$F NMR (470 MHz, CDCl$_3$) Delta: 19.0 (s); FT-IR (KBr, cm$^{-1}$): 3413, 1712, 1656, 1648, 1585, 1539; UV-Vis (CH$_3$OH,nm) Lamda max: 476 (2889), 379 (1539), 212 (14008).

Example 25

11-amino-6,11-didesoxy-6-nitrodaunomycinone

A mixture of the nitroaminonaphthacenedione(14 mg, 0.031 mmol), HgO (30 mg, 0.156 mmol), 2N H$_2$SO$_4$ (0.1 mL) and THF (1 mL) was refluxed for 30 minutes to form a pink precipitate. The reaction mixture was cooled to room temperature and the solid was collected. A solution of the solid in ethyl acetate (10 mL) was washed with 1N HCl (10 mL). The aqueous layer was re-extracted with ethyl acetate (3×10 mL). The combined organic layers were washed with saturated NaCl solution (2×10 mL) and dried (Na$_2$SO$_4$). Evaporation of the solvent gave a red solid (12 mg, 91 percent) which recrystallized from EtOAc-hexane to give 11-amino-6,11-didesoxy-6-nitrodaunomycinone as a red needles. Anal. Calcd. for C$_{21}$H$_{18}$N$_2$O$_8$:C 59.15, H 4.25, N 6.57, Found: C 59.19, H 4.60, N 6.39; $^1$H NMR (500 MHz, DMSO-d$_6$) Delta: 7.92 (d, 1H, ArH), 7.86 (t, 1H, ArH), 7.58 (s, 2H, NH$_2$), 7.55 (d, 1H, ArH), 5.97 (s, 1H, OH), 5.63 (d, 1H, OH), 4.60 (t, 1H, C$_7$H), 4.0 (s, 3H, OCH$_3$), 2.95 (d, 1H, C$_{10}$H$_e$), 2.64 (d, 1H, C$_{10}$H$_a$), 2.35 (s, 3H, CH$_3$), 2.15 (d, 1H, C$_8$H$_e$), 1.95 (dd, 1H, C$_8$H$_a$); $^{13}$C NMR (125 MHz, DMSO-d$_6$) Delta: 211.1, 183.7, 181.5, 159.6, 149.6, 145.4, 136.7, 134.9, 132.8, 125.4, 120.8, 118.6, 117.7, 114.9, 109.8, 76.4, 65.8, 56.3, 40.0, 33.5, 23.9; FT-IR (KBr, cm$^{-1}$): 3442, 3304, 1715, 1636, 1616, 1581, 1531; UV-Vis (CH$_3$OH, nm) Lambda max: 471, 430, 253, 221.

Example 26

Methyl 2alpha,3alpha-expoxy-5alpha-hydroxy-5beta-trimethylsilythynylcyclohexane-1alpha carboxylate.

Activated molecular sieves (4A, 0.5 g) and Ti(i-PRO)4 (16.9 mg, 0.06 mmol) were added to a solution of methyl 5-hydroxy-5-trimethylsilythynyl-cyclohex-2-enecarboxylate (300 mg, 1.19 mmol) in benzene (5 ml). The mixture was stirred for 30 minutes under nitrogen, cumene, hydroperoxide (80%, 0.5 mL, 2.63 mmol) was then added at 0 degrees Celsius. The reaction mixture was stirred at room temperature for 30 hours until TLC showed no starting material remained. The mixture was cooled to 0 degrees Celsius and (CH$_3$)$_2$S (192 mL, 163 mg, 2.63 mmol) was added. After the mixture had been stirred at room temperature for 30 minutes, it was filtered and the solid residue was washed with ether (20 mL). The combined organic solutions were evaporated to give an oil. The crude oil was chromatographed on silica (60–200 mesh); elution with ethyl acetate/ hexane (25/75), yielded methyl 2alpha,3alpha-epoxy-5alpha-hydroxy-5beta-trimethylsilyethynylcyclohexanecarboxylate (273 mg, 86%) as white crystals. The spectroscopic data showed that the product was identical with that obtained using t-butyl hydroperoxide (Example 4).

Example 27

Methyl 5beta-ethynyl-3alpha,5alpha-dihydroxy-1-cyclohexene-1-carboxylate.

Sodium methoxide (410 mg, 76 mmol) was added to a mixture of methyl-5alpha-hydroxy-5beta trimethylsilylethynyl-2alpha,3alpha-epoxycyclohexane-1alpha-carboxylate (2.01 g, 75 mmol) and methanol (20 mL) and stirred at room temperature overnight. The mixture was neutralized to pH 7 and extracted with ethyl acetate (5×50 mL) The combined extracts were washed with aqueous saturated NaCl solution (50 mL), dried over Na$_2$SO$_4$, passed through a short plug of silica and eluted with ethyl acetate (100 mL). Evaporation of the solvent gave methy15beta-ethynyl-3alpha,5alpha-dihydoxy-1-cyclohexene-1-carboxylate (1.4 g, 96%) as white crystals:mp:111–112 degrees Celsius; $^1$H NMR (500 MHz, CDCl$_3$, ppm): 7.03 (m, 1H, =CH), 4.35 (m, W$_{1/2}$=11 Hz, J$_{H2-H3}$=3.23 Hz, C$_3$—H), 3.80 (s, 3H, OCH$_3$), 2.82 (dd, 1H) 2.67 (bs, 2H, OH), 2.60 (dt, 1H), 2.55 (s, 1H, =CH), 2.30 (dq, 1H,);

13C NMR (125 mHz, CDCl$_3$ ppm): 167.12, 138.01, 127.51, 88.96, 72.41, 66.29, 64.51, 51.99, 41.58, 38.35; FT-IR (KBr, cm$^{-1}$): 3406 (b, OH), 3290 (≡CH, 2110 (C≡C), 1716 (C═O), 1652.

Example 28

Methyl-3beta-ethynyl-3alpha,5alpha-dihydroxy-6alpha-nitromethyl-cyclohexane-1beta-carboxylate.

1,8-diazabicyclo-[5,4,0]-undec-7-ene (DBU, 0.95 g, 6.26 mmol) was added to a mixture of methyl 3alpha,5alpha-dilhydroxy-5beta-ethynyl-1-cyclohexene carboxylate (1.28 g, 6.53 mmol) in CH$_3$NO$_2$ (5 mL) and DMSO (3 mL) at 0 degrees Celsius. This was stirred at room temperature for 12 hours, when TLC showed that all the starting diol had disappeared. HCL (50 mL. 0.1N) was added at 0 degrees Celsius. The mixture was extracted with ethyl acetate (4×30 mL). The combined extracts were washed with saturated aqueous NaCl solution (2×30 mL). Evaporation of the solvents yielded light yellow liquid (1.94 g). The crude product was chromatographed (60–200 mesh flash silica), eluting with 50/50 ethyl acetate and hexane to give two products. The first product was obtained as colorless crystals of methyl 3beta-ethynyl-3alpha, 5alpha-dihydroxy-6alpha-nitromethyl-cyclohexane-1beta-carboxylate (0.6 g 39.2%), m.p. 99–100 degrees Celsius (recrystallized from ethyl acetate and hexane); FT-IR (KBr, cm$^{-1}$): 3480 (OH), 3280 (≡CH), 1720 (C═O), 1542 (NO$_2$); $^1$H NMR (500 MHz, CDCl$_3$) delta: 4.62 (dd, J$_{gem}$=12.3 Hz J$_{HCNO2-H6e}$=8.06 Hz, 1H, CHNO$_2$), 4.49 (dd, J$_{gem}$=12.3 Hz, J$_{HCNO2-H6e}$=6.54 Hz, 1H, CHNO$_2$). 4.12. (q.J$_{H5e-H4e}$=4.43 Hz, J$_{H5e-H4a}$=4.43 Hz, J$_{H5e-H6e}$=4.83 Hz, 1H, C$_5$H$_e$), 3.71 (s, 3H, OCH$_3$). 3.50 (b, 2H, 2OH), 3.32 (m, J$_{H1a-H2a}$=8.87 Hz, J$_{H1a-H2e}$=4.84 Hz, J$_{H1a-H6e}$=4.43 Hz, 1H, OOCCH), 2.89 (m, 1H, C$_{6H}$e), 2.54 (s, 1H, ≡CH), 2.08 (m, 2H, C$_4$H$_e$C$_{2He}$JH4e-H5e=4.43 Hz, JH2e-H1a=4.84 Hz), 2.07 (m, 2H, C4Ha, C2Ha, JH4a-H5e= 4.43 Hz, J$_{H2a-H1a}$=8.86 Hz); $^{13}$C NMR (75 MHz, CDCl$_3$) delta: 173.16, 85.5, 74.34, 73.12, 67.42, 66.67, 52.11, 41.31, 41.22, 37.54, 36.11. The cis isomer has also isolated.

Example 29

Methyl-3beta-ethynyl-3alpha,5alpha-dihydroxy-6alpha-nitromethyl-cyclohexane-1beta-carboxylate 1.8-diazabicyclo-[5,4,0]-undec-7ene(DBU), 54, ul, 0.33 mmol) was added to a mixture of methyl 3alpha,5alpha-dihydroxy-5beta-ethynyl-1-cyclohexene carboxylate (65 mg, 0.33 mmol) in CH$_3$NO$_2$ (2 mL) and (CH$_3$)$_3$NO (161 mg, 1.99 mmol) at 0 degrees Celsius. This was stirred at room temperature for 4 hours, when TLC showed that all the starting diol had disappeared. HCL (5 mL, 0.1N) was added 0 degrees Celsius. The mixture was extracted with ethyl acetate (4×5 mL). The combined extracts were washed with saturated aqueous NaCl solution (2×10 mL). Evaporation of the solvents yielded light yellow liquid (90 mg). The crude product was chromatographed (60–200 mesh flash silica), eluting with 50/50 ethyl acetate and hexane to give two products. The first product was obtained as colorless crystals of methyl 3beta-ethynyl-3alpha,5alpha-dihydroxy-6alpha-nitromethyl-cyclohexane-1beta-carboxylate (33 mg, 39%), Mp. 99–100 degrees Celsius (recrystallized from ethyl acetate and hexane). The spectroscopic data on this compound is identical with that of Example 28.

Example 30

Methyl 3beta-ethynyl-3alpha,5alpha-(di-O-Isopropylidenyl-6alpha-nitromethyl-cyclohexane-1alpha-carboxylate.

To a solution of methyl 3beta-ethynyl-3alpha, 5alpha-dihydroxy-6alpha-nitromethyl cyclohexane-1beta-carboxylate (1.5 g, 5.84 mmol) in benzene (50 ml), pyridium tosylate (PPTS, 5 mg) 2-methyoxypropene (5.9 mmol) was added and the mixture was kept at room temperature until TLC shown that all starting material was gone (about 15 min). Then additional 2-methoxypropene (0.5 ml, 4.9 mmol) was and the mixture was refluxed for 5 minutes. The reaction solution was cooled to room temperature, and saturated aqueous $NaHCO_3$ solution (15 mL) was added. The aqueous layer was extracted with ethyl acetate (2×20 mL), the combined organic layers were washed with saturated aqueous NaCl solution (2×20 mL) and dried over ($Na_2SO_{4}$). The solvent was removed in vacuo. The light yellow residue was passed through a short plug of silica and eluted with ethyl acetate and hexane (25:75, 200 ml) to afford methyl 5beta-ethynyl-3alpha,5alpha-(di-O-isopropylidenyl)-6alpha-nitromethyl-cyclohexane-1beta-carboxylate as a colorless oil.

The preceding examples can be repeated with similar success by substituting the generically or specifically described reactants and/or operating conditions of this invention for those used in the preceding examples.

Although preferred embodiments of the invention have been described with some particularity, many modifications and variations in the preferred embodiment are possible without deviating from the invention. Is it therefore to be understood that, within the scope of the appended claims, the invention may be practiced other than as specifically described.

What is claimed is:

1. A process for the production of daunomycinone, or its 6-desoxy-6-nitro, 6-desoxy-6-amino, 6 desoxy-6-cyano, 6-desoxy, or 6-halo-6-desoxy analogues comprising the steps of:

condensing the acetonide of methyl 3alpha,5alpha-dihydroxy-5beta-(trimethylsilylethynyl)-2alpha-nitromethylcyclohexane-1alphacarboxylate with 1,4-dihydro-4, 4,5-trimethoxy-1-oxonaphthalene in the presence of 1,8-diazabicyclo [5.4.0]undec-7-ene in the presence of a hydrogen bond acceptor to produce 3 -[2beta-carbomethoxy-4beta-ethynyl-4alpha,6alpha-(di-O-isopropylidenyl)cyclohexan-1-yl]-nitromethyl-4,4,5-trimethoxy-1-oxo-1,2,3,4-tetrahydronaphthalene; and cyclizing said 1-oxotetrahydronaphthalene to produce 7alpha,9alpha-(di-O-isopropylidenyl)-9beta-ethynyl-12-hydroxy-6-nitro-4,5,5-trimethoxy-5,5a,6, 6a,7,8,9, 10,10a,11-decahydro-11-naphthacenone;

the step of cyclizing said 1-oxotetrahydronaphthalene including the steps of converting said decahydro-11-naphthacenone to 7alpha,9alpha-(di-O-isopropylidenyl)-4,5-dimethoxy-9beta-ethynyl-12-hydroxy-6-nitro-6,6a,7,8,9,10,10a, 11-octahydro-11-naphthacenone, oxidizing said octahydro-11-naphthacenone to 7alpha, 9alpha-(di-O-isopropylidenyl)-9beta-ethynyl-11-hydroxy-4-methoxy-6-nitro-7,8,9,10-tetrahydro-5,12-naphthacenedione, hydrolysing said 5,12-naphthacenedione to 6-desoxy-6-nitrodaunomycinone, reducing said nitronaphthacenedione to 6-amino-7alpha,9alpha-(di-O-isoproylidenyl)-9beta-ethynyl-11-hydroxy-4-methoxy-7,8,9,10-tetrahydro-5,12-naphthacenedione, and converting said aminonaphthacenedione by way of the 6-diazonium derivatives to daunomycinone, 6-desoxydaunomycinone, the 6-desoxy-6-halodaunomycinones, or said analogues.

2. The process of claim 1 wherein 1-oxotetrahydronaphthalene is cyclized with an alkali metal alkoxide of 1–6 carbon atoms.

3. The process of claim 1 wherein said decahydro-11-naphthacenone is converted to 7alpha,9alpha-(di-O-isopropylidenyl)-4,5-dimethoxy-9beta-ethynyl-12-hydroxy-6-nitro 6,6a,7,8,9,10,10a, 11-octahydro-11-napthacenone under acidic conditions.

4. The process of claim 1 wherein said octahydro-11-naphthacenone is oxidized to 7alpha, alpha-(di-O-isopropylidenyl)-9beta-ethynyl-11-hydroxy-4-methoxy-6-nitro-9 7,8,9,10-tetrahydro-5,12-naphthacenedione with a reagent selected from a group consisting of cerium ammonium nitrate, thallium trinitrate, and iodobenzenediacetate, using with each oxidant a catalytic quantity of 2,3-dichloro-5,6-dicyanobenzoquinone.

5. A process for the production of derivatives of daunomycinone, comprising the steps of:

condensing the acetonide of methyl 3alpha,5alpha-dihydroxy-5beta-(trimethylsilylethynyl)-2alpha-nitromethylcyclohexane-1alpha-carboxylate with 1,4-dihydro-4, 4,5-trimethoxy-1-oxonaphthalene in the presence of 1,8-diazabicyclo[5.4.0]undec-7-ene in an aprotic solvent to produce 3-[2beta-carbomethoxy-4beta-ethynyl-4alpha,6alpha-(di-O-isopropylidenyl)cyclohexan-1-yl] -nitromethyl-4,4,5-trimethoxy-1-oxo-1,2,3,4-tetrahydronaphthalene; and cyclizing said 1-oxotetrahydronaphthalene to produce 7alpha,9alpha-(di-O-isopropylidenyl)-9beta-ethynyl-12-hydroxy-6-nitro-4,5,5-trimethoxy-5,5a,6,6a,7,8,9, 10,10a,11-decahydro-11-naphthacenone characterized by converting said decahydro-11-naphthacenone to 7alpha,9alpha-(di-O-isopropylidenyl)-4,5-dimethoxy-9beta-ethynyl-12-hydroxy-6-nitro-6,6a,7,8,9,10,10a, 11-octahydro-11-naphthacenone; converting said octahydro-11-naphthacenone to 7alpha,9alpha-(di-O-isopropylidenyl)-11-imino-6-nitro-6,6a,7,8,9,10,10a, 11-octahydronaphthacene with methanol and ammonia; oxidizing the 7alpha,9alpha-(di-O-isopropylidenyl)-9beta-ethynyl-11-imino-6-nitro-6,6a, 7,8,9,10,10a,11-octahydronaphthacene to 11-amino-7alpha,9alpha-(di-O-isopropylidenyl)-9beta-ethynyl-4-methoxy-6-nitro-7,8,9,10-tetrahydro-5,12-naphthacenedione with cerium ammonium nitrate and a catalytic amount of dichlorodicyanobenzoquinone or $O_2/DMF$; hydrolyzing hydrating the 11-amino-7alpha,9alpha-(di-O-isopropylidenyl)-9beta-ethynyl-4-methoxy-6-nitro-7,8,9,10-tetrahydro-5,12-naphthacenedione to 11-amino-6,11-didesoxy-6-nitrodaunomycinone with acid and mercuric oxide; converting aminonitrodaunomycinone by the diazonium salt to 6,11-didesoxy-6-nitrodaunomycinone; reducing said 11-amino-6-nitronaphthacenedione with stannous chloride in methanol to 6,11-diamino-7alpha,9alpha-(di-O-isopropylidenyl)-9beta-ethynyl-4-methoxy-7,8,9,10-tetrahydro-5,12-naphthacenedione; hydrolyzing and hydrating said diamino naphthacenedione to 6,11-diamino 6,11-didesoxy daunomycinone.

6. A process according to claim 5 wherein the 6,11-diamino-7alpha,9alpha-(di-O-isopropylidenyl)-9beta-ethynyl-4-methoxy-7,8,9,10-tetrahydro-5,12-naphthacenedione is converted to 6,11-diamino-6,11-didesoxydaunomycinone using HgO under acidic conditions.

7. A process according to claim 6 wherein the 11-amino-6,11-didesoxy-6-nitrodaunomycinone is converted into an 11-halo derivative through the 11-diazonium-6-nitrodaunomycinone;

the 11-halo is converted to a selected one of the groups consisting of 6-hydroxy-11-fluoro, 11-chloro, 11-bromo and 11-iodo daunomycinones by way of the 6-diazonium compound; and the 6-diazonium compounds of the 11-halo compounds are converted to the corresponding one of the 11-halo-6-fluoro, 6-chloro, 6-bromo and 6-iodo daunomycinones.

8. A process of synthesizing methyl cis-3,5-dihydroxy-5-(trimethylsilylethynyl)cyclohex-1-ene-1-carboxylate and methyl cis 3,5-dihydroxy-5-ethynyl cyclohex-1-ene-1 carboxylate from m-anisic acid characterized by Birch reduction with lithium in ammonia to produce 5-oxocyclohex-2-ene-1-carboxylic acid, methylation of said cyclohex-2-ene-1-carboxylic acid to methyl 5-oxo-cyclohex-2-ene-1-carboxylate with diazomethane, trimethylsilylethynylation of said cyclohex-2-ene-1-carboxylate with cerium dichloride trimethylsilylacetylene to produce methyl cis-5-hydroxy-5-(trimethylsilylethynyl)cyclohex-2-ene-1-carboxylate, and conversion to an epoxide and opening of the resulting epoxide ring to give said cyclohex-1-ene-1-carboxylates.

9. The process of claim 8 characterized in that the reaction mixture is kept cold during esterification with diazomethane and the ethanol that is present in the esterification reaction mixture is removed by azeotropic distillation with benzene, methyl ester is treated with cerium dichloride trimethylsilylacetylene at a low temperature to prevent formation of a lactone, the epoxide is formed by oxidation with t-butyl hydroperoxide in the presence of molybdenum hexacarbonyl catalyst and molecular sieves or by oxidation with cumyl hydroperoxide catalysed by titanium tetraisopropoxide and isolating the thus-produced epoxide and the epoxide ring is opened with 1,8-diazabicyclo[5.4.0]-undec-7-ene or 1,5-diazabicyclo[4.3.0]non-5-ene or sodium methoxide in methanol; the latter conditions also remove the trimethysilyl group to give methyl cis3,-5-dihydroxy-5-ethynylcyclohex-1-ene-1-carboxylate.

10. 3,5-acetonide of methyl 3alpha,5alpha-dihydroxy-5beta-(tri-methylsilylethynyl)-2alpha-nitromethylcyclohexane-1beta-carboxylate.

11. A process for producing methyl 3alpha,5alpha-dihydroxy-5beta-ethynyl-2alpha-nitromethylcyclohexane-1beta-carboxylate comprising the steps of reacting methyl cis-3,5-dihydroxy-5-beta-ethynylcyclohex-1-ene-1-carboxylate with nitromethane in the presence of 1,8-diazabicyclo[5.4.0]undec-7-ene or 1,5-diazabicyclo[4.3.0]non-5-ene or sodium hydride or potassium hydride in an aprotic solvent which can form hydrogen bonds with hydroxyl groups.

12. A process for preparing methyl 3-alpha,5-alpha-dihydroxy-5-beta-(trimethylsilylethynyl)-2alpha-nitromethylcyclohexane-1-beta-carboxylate characterized by reacting methyl cis-(2,3alpha-epoxy-5alpha-hydroxy-5beta-(trimethylsilylethynyl)cyclohexane-1alpha-carboxylate with nitromethane in the presence of 1,8-diazabicyclo[5.4.0]undec-7-ene in the presence of a substance that can form hydrogen bonds with hydroxyl groups.

13. A compound of the general formula:

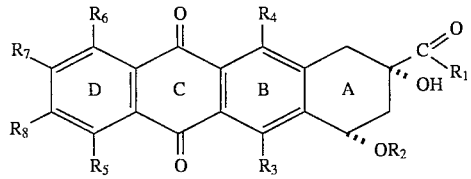

wherein $R_1$ is one of: $CH_3$ or $CH_2OH$;

$R_2$ is one of daunosamine, or H;

$R_3$ is one of OH, $NO_2$, $NH_2$, F, Cl, Br, I, CN and H or groups derived from these;

$R_4$ is one of $NO_2$, $NH_2$, F, Cl, Br, I and CN or groups derived or substituted for these; and $R_5$ is $OCH_3$, OH or H;

$R_5$, $R_6$, $R_7$ are all H or $R_5$ and $R_6$ are H and $R_7$ and $R_8$ are alkyl or halo; or $R_5$ and $R_6$ are alkyl or halo and $R_7$ and $R_8$ are H.

14. A compound according to claim 13 wherein the compound is 11-amino-6,11-didesoxy-6-nitrodaunomycinone.

15. A compound according to claim 13 wherein the compound is 6,11-diamino-6,11-didesoxydaunomycinone.

16. A compound according to claim 13 wherein the compound is a 11-halo derivative.

17. A compound according to claim 13 wherein the compound is a 11-cyano derivatives.

18. A compound according to claim 13 wherein the compound is a compound selected from the group consisting of the 11-halo and 11-cyano-6-nitrodaunomycinones.

19. A compound according to claim 10 wherein the compound is a 11-flourine derivative.

20. A compound according to claim 13 wherein the compound is selected from the group of compounds consisting of 6,11-difluro, 6,11-dichloro, 6,11-dibromo, 6,11-diiodo and 6,11-dicyano daunomycinones.

21. Methyl 3alpha,5alpha-dihydroxy-5beta-(trimethylsilylethynyl)-2alpha-nitromethylcyclohexane-1beta-carboxylate.

22. A process according to claim 6 wherein one of:

the 11-amino-6,11-didesoxy-6-nitrodaunomycinone is converted into an 11-cyano derivative through the 11-diazonium-6-nitrodaunomycinone;

the 6-diazonium compounds of the cyano compounds are converted to 6-cyano daunomycinone.

23. A process according to claim 7 wherein 6,11-diamino-6,11-didesoxydaunomycinone is converted to a selected compound from the group consisting of 6,11-difluro, 6,11-dichloro, 6,11-dibromo, 6,11-diiodo and 6,11-dicyano daunomycinones.

* * * * *